US007439320B2

(12) United States Patent
Cassart et al.

(10) Patent No.: US 7,439,320 B2
(45) Date of Patent: Oct. 21, 2008

(54) CRIPTO TUMOUR POLYPEPTIDE

(75) Inventors: Jean-Pol Cassart, Rixensart (BE); Thierry Coche, Rixensart (BE); Remi M Palmantier, Rixensart (BE); Carlota Vinals Y De Bassols, Rixensart (BE)

(73) Assignee: GlaxoSmith Kline Biologicals s.a., Rixensart (BE)

( * ) Notice: Subject to any disclaimer, the term of this patent is extended or adjusted under 35 U.S.C. 154(b) by 558 days.

(21) Appl. No.: 10/362,597

(22) PCT Filed: Aug. 20, 2001

(86) PCT No.: PCT/EP01/09646

§ 371 (c)(1),
(2), (4) Date: Aug. 4, 2003

(87) PCT Pub. No.: WO02/16413

PCT Pub. Date: Feb. 28, 2002

(65) Prior Publication Data

US 2004/0054142 A1 Mar. 18, 2004

(30) Foreign Application Priority Data

Aug. 24, 2000 (GB) ................................ 0020953.6

(51) Int. Cl.
*A61K 38/00* (2006.01)

(52) U.S. Cl. ...................................................... 530/300

(58) Field of Classification Search ................. 530/350, 530/300

See application file for complete search history.

(56) References Cited

U.S. PATENT DOCUMENTS

| | | | | |
|---|---|---|---|---|
| 5,256,643 | A * | 10/1993 | Persico et al. | 514/12 |
| 5,633,147 | A * | 5/1997 | Meissner et al. | 435/69.1 |
| 5,854,399 | A | 12/1998 | Salomon et al. | |
| 6,270,777 | B1 * | 8/2001 | Sokol et al. | 424/260.1 |

FOREIGN PATENT DOCUMENTS

| | | |
|---|---|---|
| WO | WO 00/06723 | 2/2000 |
| WO | WO 01/94629 | 12/2001 |
| WO | WO 02/077033 | 10/2002 |

OTHER PUBLICATIONS

Sloane et al (Journal of Biotechnology, 1996, 49:231-238).*
Lederman et al (Molecular Immunology 28:1171-1181).*
Sloane (Journal of Biological Chemistry, 1996, 49:231-238).*
Baldassarre et al., Transfection with a Cripto anti-Sense Plasmid Suppresses Endogenous Cripto Expression and Inhibits Transformation in a Human Embronal Carcinoma Cell Line, Int. J. Cancer 4(66):538-543 (1996).
Brandt et al., Indentification and biological Characterization of an Epidermal Growth Factor-Related Protein: Cripto-1, J. of Biological Chemistry 269(25):17320-17328 (1994).
Ciardiello et al., Differental Expression of Epidermal Growth Factor-Related Proteins in Human Colorectal Tumors, Proc. Natl. Acad. Sci. USA 88:7792-7796 (1991).
Ciardiello et al., Inhibition of CRIPTO Expression and Tumorigenicity in Human Colon Cancer Cells by Antisense RNA and Oligodeoxynucleotides, Onocgene 9:291-298 (1994).
Fontanini et al., Evaluation of Epidermal Growth Factor-related Growth Factors and Receptors and of Neoangiogenesis in Completely Resected Stage I-ILA Non-Small-Cell Lung Cancer: Amphiregulin and Microvessel Count are Independent Prognostic Indicators of Survival, Clinical Cancer Research 4:241-249 (1998).
Normanno et al., Growth Inhibition of Human Colon Carcinoma Cells by Combinations of Anti-Epidermal Growth Factor-related Growth Factor Antisense Olignoucleotides, Clinical Cancer Research 2:601-609 (1996).
Panico et al., Differential Immunohistochemical Detection of Transforming Growth Factor α, Amphiregulin and Cripto in Human Normal and Malignant Breast Tissues, Int. J. Cancer 65:51-56 (1996).
Saiki et al., Differential Immunohistochemical Detection of Amphiregulin and Cripto in Human Normal colon and Colorectal Tumors, Cancer Research 52:3467-3473 (1992).
Seno et al., Purification and Characterization of a Recombinant Human Cripto-1 Protein, Growth Factors 15:215-229.
PCT International Search Report.

* cited by examiner

*Primary Examiner*—Misook Yu
*Assistant Examiner*—Sean Aeder
(74) *Attorney, Agent, or Firm*—Eric J. Kron

(57) ABSTRACT

Compositions and methods for the therapy and diagnosis of cancer, particularly lung, colon, colorectal and breast cancer, are disclosed. Illustrative compositions comprise one or more Cripto tumor polypeptides, immunogenic portions thereof, polynucleotides that encode such polypeptides, antigen presenting cell that expresses such polypeptides, and T cells that are specific for cells expressing such polypeptides. The disclosed compositions are useful, for example, in the diagnosis, prevention and/or treatment of diseases, particularly lung, colon, colorectal and breast cancer.

3 Claims, 5 Drawing Sheets

Fig. 1 RT-PCR expression analysis of Cripto on colorectal cancer patients, Sybrl detection (T indicates tumor colon, N indicates matched normal tissue).
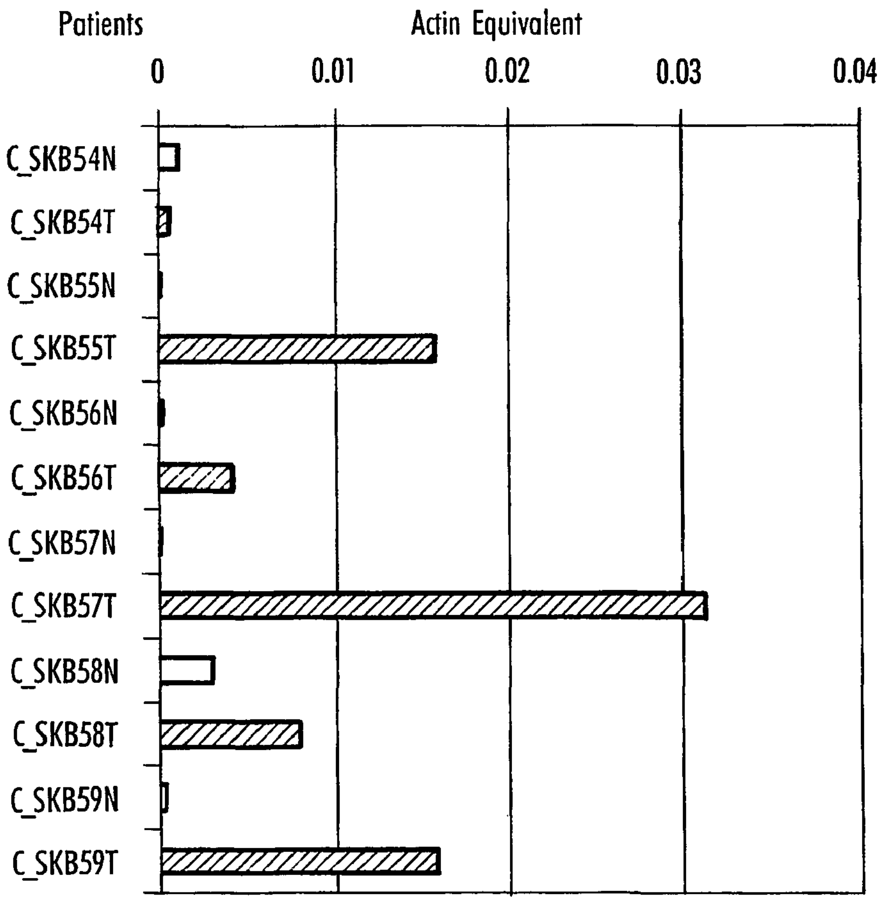

Fig. 2 RT-PCR expression analysis of Cripto on colorectal cancer patients, TaqMan detection (T indicates tumor colon, N indicates matched normal tissue).
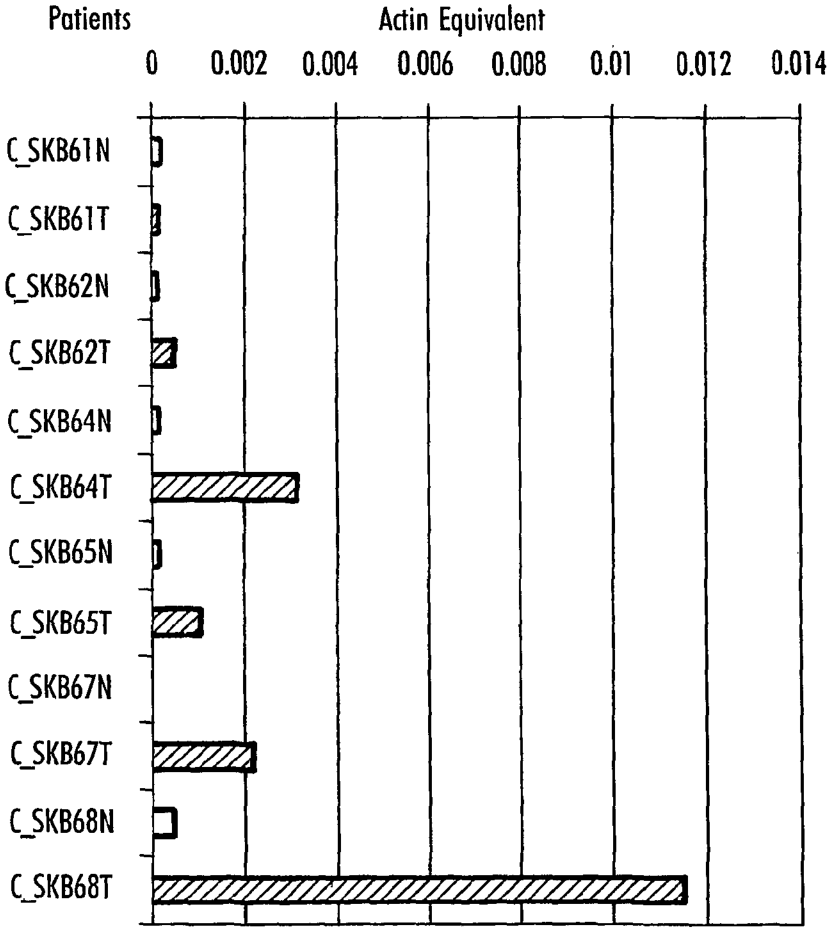

Fig. 3 RT-PCR expression analysis of Cripto on a panel of normal tissues, Sybrl detection.
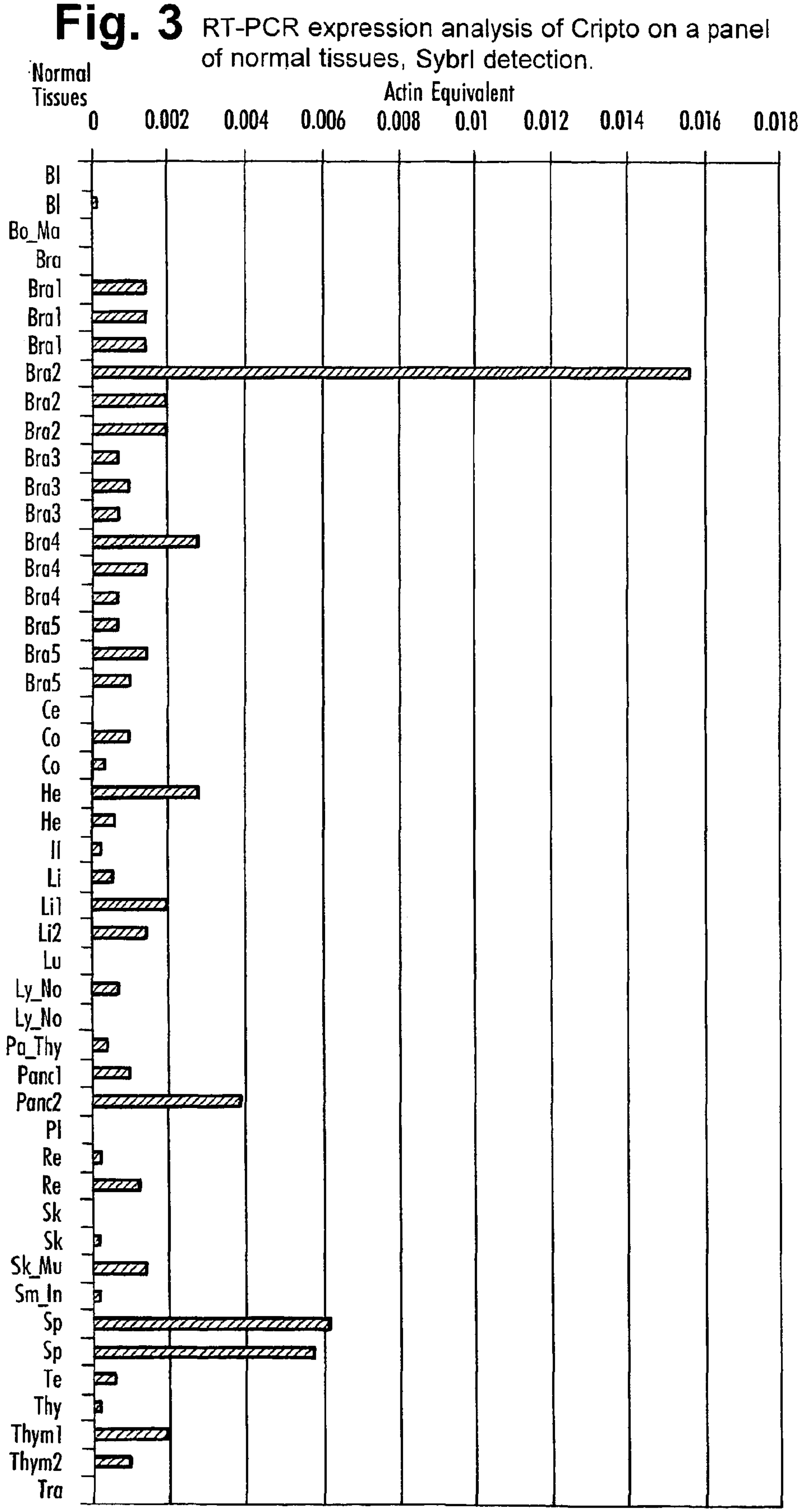

Fig. 4 RT-PCR expression analysis of Cripto on a panel of normal tissues, TaqMan detection.
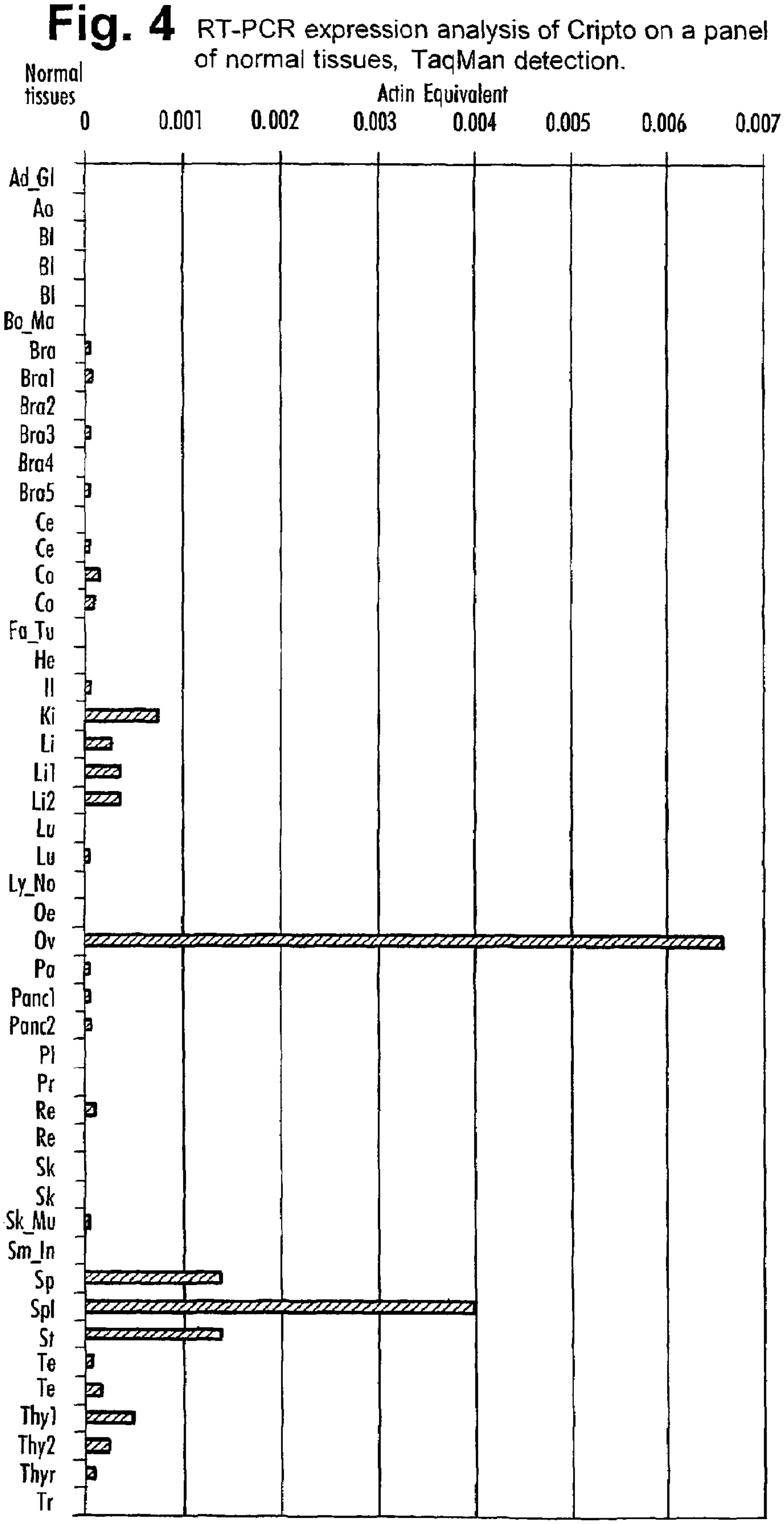

Fig. 5 RT-PCR expression analysis of Cripto on a panel of cell lines.
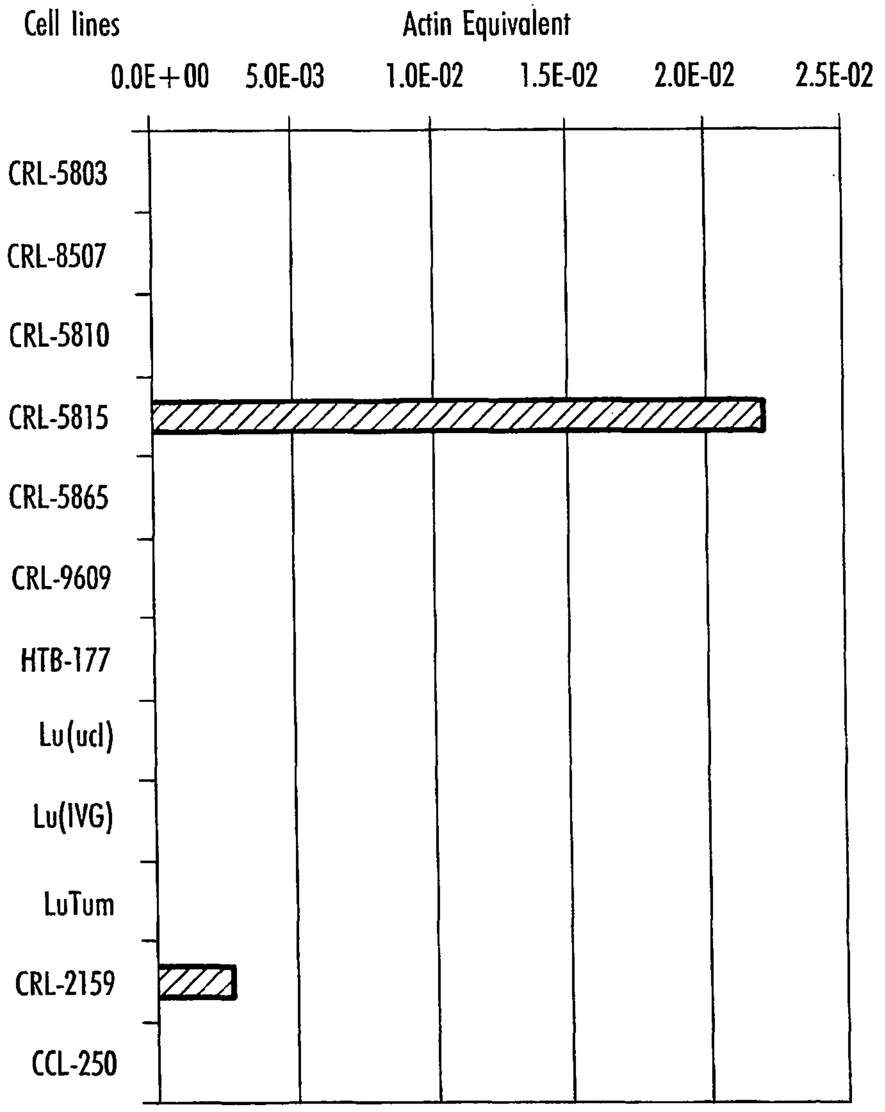

CRIPTO TUMOUR POLYPEPTIDE

This is the national phase under 35 U.S.C. § 371 of PCT International Application PCT/EP01/09646, filed 20 Aug. 2001, which claims benefit from Great Britain Application No.: GB 0020953.6, filed 24 Aug. 2000.

TECHNICAL FIELD OF THE INVENTION

The present invention relates generally to therapy of cancer, such as colon, colorectal, breast, bladder, lung and endometrial cancer. The invention is more specifically related to polypeptides, comprising at least a portion of a cripto protein tumor protein, and to polynucleotides encoding such polypeptides, in particular pharmaceutical compositions, e.g., vaccines, and other compositions for the treatment of cancer that are cripto—expressing carcinomas such as certain non-small long cell carcinoma, breast, colon, colorectal cancer.

BACKGROUND OF THE INVENTION

CRIPTO is a 188 aa protein shares homologies with the epidermal growth factor (EGF) family (EMBO Journal (1989) Vol 8 (7) pp1987-1991).

huCRIPTO mRNA is detected only in undifferentiated cells and disappear after cell differentiation mCRIPTO is expressed during pregnancy and lactation (induces branching morphogenesis in mammary epithelial cells) and is suspected to be an autocrine growth factor for normal breast cells. CRIPTO is required for correct orientation of the anterior-posterior axis in the mouse embryo.

Human cripto gene has been expressed U.S. Pat. No. 5,654,140.

Cancer is a significant health problem throughout the world. Although advances have been made in detection and therapy of cancer, no vaccine or other universally successful method for prevention and/or treatment is currently available. Current therapies, which are generally based on a combination of chemotherapy or surgery and radiation, continue to prove inadequate in many patients.

Colon cancer is the second most frequently diagnosed malignancy in the United Sates as well as the second most common cause of cancer death. An estimated 95,600 new cases of colon cancer will have been diagnosed in 1998, with an estimated 47,700 deaths. The five-year survival rate for patients with colorectal cancer detected in an early-localised stage is 92%, unfortunately, only 37% of colorectal cancer is diagnosed at this stage. The survival stage. The survival rate drops to 64% if the cancer is allowed to spread to adjacent organs or lymph nodes, and to 7% in patients with distant metastases.

The prognosis of colon cancer is directly related to the degree of penetration of the tumour through the bowel wall, to the level of metastasis, to the presence or absence of nodal involvement, consequently, early detection and treatment are especially important. Currently, diagnosis is aided by the use of screening assays for fecal occult blood, sigmoidoscopy, colonoscopy and double contrast barium enemas. Treatment regimens are determined by the type and stage of the cancer, and include surgery, radiation therapy and/or chemotherapy. Recurrence following surgery (the most common form of therapy) is a major problem and is often the ultimate cause of death. In spite of considerable research into therapies for the disease, colon cancer remains difficult to diagnose and treat.

Accordingly, there is a need in the art for improved methods for treating such cancers. The present invention fulfils these needs and further provides other related advantages.

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the lifetime odds of getting breast cancer are now one in eight.

No vaccine or other universally successful method for the prevention or treatment of breast cancer is currently available. Management of the disease currently relies on a combination of early diagnosis (through routine breast screening procedures) and aggressive treatment which may including one or more of a variety of treatments such as surgery, radiotherapy, chemotherapy and hormone therapy. The course of treatment for a particular breast cancer is often selected based on a variety of prognostic parameters, including an analysis of specific tumour markers. See, eg Porter-Jordan and Lippman, Breast Cancer 8:73-100 (1994). However, the use of established markers often leads to a result that this is difficult to interpret, and the high mortality observed in breast cancer patients indicates that improvements are needed in the treatment and prevention of the disease.

Lung cancer is the primary cause of cancer death among both men and women in the US, with an estimated 172,000 new cases being reported in 1994. The five-year survival rate among all lung cancer patients, regardless of the state of disease at diagnosis is only 13%. This contrasts with a five-year survival rate of 46% among cases detected while the disease is still localised. However, only 16% of lung cancers are discovered before the disease has spread.

In spite of considerable research into therapies for these and other cancers, breast, colon and colorectal remains difficult to diagnose and treat effectively. Accordingly, there is a need in the art for improved methods for treating and preventing such cancers. The present invention fulfills these needs and further provides other related advantages.

SUMMARY OF THE INVENTION

In one aspect, the present invention provides polynucleotide compositions comprising a sequence selected from the group consisting of:

(a) sequences consisting of at least 20 contiguous residues of a sequence provided in SEQ ID NO: 1 or 3 not being the full sequence of ID NO:1 or 3.

(b) sequences consisting of Sequence ID NO: 1 or 3 or sequences that consist of at least 20 contiguos nucleotides provided in Seq ID No 1 or 3 and a polynucleotide that encodes for a heterologous fusion partner.

The present invention, in another aspect, provides polypeptide compositions comprising an amino acid sequence that is encoded by a polynucleotide sequence described above.

The polypeptides and/or polynucleotides of the present invention are immunogenic, i.e., they are capable of eliciting an immune response, particularly a humoral and/or cellular immune response, when if necessary, they are conjugated to a suitable carrier and/or adjuvanted.

The present invention further provides fragments, variants and/or derivatives of the disclosed polypeptide and/or polynucleotide sequences, wherein the fragments, variants and/or derivatives preferably have a level of immunogenic activity of at least about 50%, preferably at least about 70% and more preferably at least about 90% of the level of immunogenic activity of a polypeptide sequence set forth in SEQ ID No: 2 or 4 or a polypeptide sequence encoded by a polynucleotide sequence set forth in SEQ ID NO: 1 or 3.

The present invention further provides polynucleotides that encode a polypeptide described above, expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, the pharmaceutical compositions, e.g., vaccine compositions, are provided for prophylactic or therapeutic applications. Such compositions generally comprise an immunogenic polypeptide or polynucleotide of the invention and an immunostimulant, such as an adjuvant.

Within further aspects, the present invention provides pharmaceutical compositions comprising: (a) an antigen presenting cell that expresses a polypeptide as described above and (b) a pharmaceutically acceptable carrier or excipient. Illustrative antigen presenting cells include dendritic cells, macrophages, monocytes, fibroblasts and B cells.

Within related aspects, pharmaceutical compositions are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins, typically in the form of pharmaceutical compositions, e.g., vaccine compositions, comprising a physiologically acceptable carrier and/or an immunostimulant. The fusion proteins may comprise multiple immunogenic polypeptides or portions/variants thereof, as described herein, and may further comprise one or more polypeptide segments for facilitating the expression, purification and/or immunogenicity of the polypeptide(s).

Within further aspects, the present invention provides methods for stimulating an immune response in a patient, preferably a T cell response in a human patient, comprising administering a pharmaceutical composition described herein. The patient may be afflicted with lung or colon cancer or colorectal cancer or breast cancer, in which case the methods provide treatment for the disease, or patient considered at risk for such a disease may be treated prophylactically. In particular the patient will be afflicted with a tumour expressing cripto antigens.

Within further aspects, the present invention provides methods for inhibiting the development of a cancer in a patient, comprising administering to a patient a pharmaceutical composition as recited above. The patient may be afflicted with lung, colon, colorectal or breast cancer, in which case the methods provide treatment for the disease, or patient considered at risk for such a disease may be treated prophylactically.

The present invention further provides, within other aspects, methods for removing tumor cells from a biological sample, comprising contacting a biological sample with T cells that specifically react with a polypeptide of the present invention, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a polypeptide of the present invention, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating CD4+ and/or CD8+ T cells isolated from a patient with one or more of: (i) a polypeptide comprising at least an immunogenic portion of a cripto polypeptide disclosed herein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

These and other aspects of the present invention will become apparent upon reference to the following detailed description. All references disclosed herein are hereby incorporated by reference in their entirety as if each was incorporated individually.

BRIEF DESCRIPTION OF THE DRAWINGS AND SEQUENCE IDENTIFIERS

SEQ ID NO: 1 Cripto 1 Polynucleotide
SEQ ID NO: 2 Cripto 3 Polynucleotide
SEQ ID NO: 2 Cripto 3 Polypeptide 1
SEQ ID NO: 3 Cripto 1 Polypeptide
SEQ ID NO: 4 Cripto 3 Polypeptide
SEQ ID NO: 5 Cripto Polynucleotide as described in US 5654 140
SEQ ID NO: 6 Cripto Polynucleotide as described in US 5654 140
SEQ ID NOS: 7-10 PCR primers
SEQ ID NOS: 11 & 12 synthetic Cripto 1 peptides
SEQ ID NOS: 13-94 Epitopes from Cripto 1 and 3
SEQ ID NO: 95 Cripto 1 variant Polynucleotide
SEQ ID NO: 96 Cripto 1 variant Polypeptide

DETAILED DESCRIPTION OF THE INVENTION

The present invention is directed generally to compositions and their use in the therapy and diagnosis of cancer, particularly cripto expressing cancer and metastases including Cripto expressing lung, colon, colorectal and breast cancers. As described further below, illustrative compositions of the present invention include, but are not restricted to, polypeptides, particularly immunogenic polypeptides, polynucleotides encoding such polypeptides, antibodies and other binding agents, antigen presenting cells (APCs) and immune system cells (e.g., T cells).

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

Polypeptide Compositions

As used herein, the term "polypeptide" is used in its conventional meaning, i.e. as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising epitopes, i.e. antigenic determinants substantially responsible for the immunogenic properties of a polypeptide and being capable of evoking an immune response Particularly illustrative polypeptides of the present invention comprise a sequence of at least 10 contiguous amino acids, preferably 20, more preferably 30, 40, 50, 60, 70, 80, 90, 100, 110, 120, 130, 140, 150, 160, 170, 180 amino acids of the cirpto protein of ID NO: 2 or 4.

In certain preferred embodiments, the polypeptides of the invention are immunogenic, i.e., they react detectably within an immunoassay (such as an ELISA or T-cell stimulation assay) with antisera and/or T-cells from a patient with cripto expressing cancer. Screening for immunogenic activity can be performed using techniques well known to the skilled artisan. For example, such screens can be performed using methods such as those described in Harlow and Lane, *Antibodies: A Laboratory Manual,* Cold Spring Harbor Laboratory, 1988. In one illustrative example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As would be recognized by the skilled artisan, immunogenic portions of the polypeptides disclosed herein are also encompassed by the present invention. An "immunogenic portion," as used herein, is a fragment of an immunogenic polypeptide of the invention that itself is immunologically reactive (i.e., specifically binds) with the B-cells and/or T-cell surface antigen receptors that recognize the polypeptide. Immunogenic portions may generally be identified using well known techniques, such as those summarized in Paul, *Fundamental Immunology,* 3rd ed., 243-247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well-known techniques.

In one preferred embodiment, an immunogenic portion of a polypeptide of the present invention is a portion that reacts with antisera and/or T-cells at a level that is not substantially less than the reactivity of the full-length polypeptide (e.g., in an ELISA and/or T-cell reactivity assay). Preferably, the level of immunogenic activity of the immunogenic portion is at least about 50%, preferably at least about 70% and most preferably greater than about 90% of the immunogenicity for the full-length polypeptide. In some instances, preferred immunogenic portions will be identified that have a level of immunogenic activity greater than that of the corresponding full-length polypeptide, e.g., having greater than about 100% or 150% or more immunogenic activity.

In certain other embodiments, illustrative immunogenic portions may include peptides in which an N-terminal leader sequence and/or transmembrane domain have been deleted. Other illustrative immunogenic portions will contain a small N- and/or C-terminal deletion (e.g., 1-30 amino acids, preferably 5-15 amino acids), relative to the mature protein.

In another embodiment, a polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof.

In another embodiment of the invention, polypeptides are provided that comprise one or more polypeptides that are capable of eliciting T cells and/or antibodies that are immunologically reactive with one or more polypeptides described herein, or one or more polypeptides encoded by contiguous nucleic acid sequences contained in the polynucleotide sequences disclosed herein, or immunogenic fragments or variants thereof, or to one or more nucleic acid sequences which hybridize to one or more of these sequences under conditions of moderate to high stringency.

The present invention, in another aspect, provides polypeptide fragments comprising at least about 5, 10, 15, 20, 25, 50, 100, or 150 contiguous amino acids, or more, including all intermediate lengths, of a polypeptide compositions set forth herein, such as those set forth in SEQ ID NO: 2 or 4 or those encoded by a polynucleotide sequence set forth in a sequence of SEQ ID NO: 1 or 3. It is preferred that the polypeptides comprise at least one preferably a pluarality of epitopes as set forth in sequence ID no 13 to 94. Optionally the frgaments are fused or otherwise conjugated to a heterologous carrier.

In another aspect, the present invention provides variants of the polypeptide compositions described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

In one preferred embodiment, the polypeptide fragments and variants provide by the present invention are immunologically reactive with an antibody and/or T-cell that reacts with a full-length polypeptide specifically set for the herein.

In another preferred embodiment, the polypeptide fragments and variants provided by the present invention exhibit a level of immunogenic activity of at least about 50%, preferably at least about 70%, and most preferably at least about 90% or more of that exhibited by a full-length polypeptide sequence specifically set forth herein.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating their immunogenic activity as described herein and/or using any of a number of techniques well known in the art.

For example, certain illustrative variants of the polypeptides of the invention include those in which one or more portions, such as an N-terminal leader sequence or transmembrane domain, have been removed. Other illustrative variants include variants in which a small portion (e.g., 1-30 amino acids, preferably 5-15 amino acids) has been removed from the N- and/or C-terminal of the mature protein.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE 1

| Amino Acids | | | Codons |
|---|---|---|---|
| Alanine | Ala | A | GCA GCC GCG GGU |
| Cysteine | Cys | C | UGG UGU |
| Aspartic acid | Asp | D | GAG GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUG AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |

TABLE 1-continued

| Amino Acids | | | Codons |
|---|---|---|---|
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Within other illustrative embodiments, a polypeptide may be a fusion polypeptide that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. New Engl. J. Med., 336:86-91, 1997).

In one preferred embodiment, the immunological fusion partner is derived from a Mycobacterium sp., such as a *Mycobacterium tuberculosis*-derived Ra12 fragment. Ra12 compositions and methods for their use in enhancing the expression and/or immunogenicity of heterologous polynucleotide/polypeptide sequences is described in U.S. Patent Application No. 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. Patent Application No. 60/158,585; see also, Skeiky et al., Infection and Immun. (1999) 67:3998-4007, incorporated herein by reference). C-terminal fragments of the MTB32A coding sequence express at high levels and remain as a soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see Biotechnology 10:795-798, 1992). Within a preferred embodiment, a repeat portion of LYTA may be incorporated into a fusion polypeptide. A repeat portion is found in the C-terminal region starting at residue 178. A particularly preferred repeat portion incorporates residues 188-305.

Yet another illustrative embodiment involves fusion polypeptides, and the polynucleotides encoding them, wherein the fusion partner comprises a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of CD4+ T-cells specific for the polypeptide.

The cripto part of the fusion molecule may prefreably be the whole length 188 aa protein of Cripto 1 or Cripto 3 or a fragment thereof as described herein.

Polypeptides of the invention are prepared using any of a variety of well known synthetic and/or recombinant techniques, the latter of which are further described below. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

In general, polypeptide compositions (including fusion polypeptides) of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

Polynucleotide Compositions

The present invention, in other aspects, provides polynucleotide compositions that encode for the polypeptides of the invention. The terms "DNA" and "polynucleotide" are used essentially interchangeably herein to refer to a DNA molecule that has been isolated free of total genomic DNA of a particular species. "Isolated," as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

As will be understood by those skilled in the art, the polynucleotide compositions of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be also recognized by the skilled artisan, polynucleotides of the invention may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide/protein of the invention or a portion thereof) or may comprise a sequence that encodes a variant or derivative, preferably and immunogenic variant or derivative, of such a sequence.

Typically, polynucleotide variants will contain one or more substitutions, additions, deletions and/or insertions, preferably such that the immunogenicity of the polypeptide encoded by the variant polynucleotide is not substantially diminished relative to a polypeptide encoded by a polynucleotide sequence specifically set forth herein). The term "variants" should also be understood to encompasses homologous genes of xenogenic origin.

In additional embodiments, the present invention provides polynucleotide fragments comprising various lengths of contiguous stretches of sequence identical to or complementary to one or more of the SEQ ID NO: 1 or 3. For example, polynucleotides are provided by this invention that comprise at least about 10, 15, 20, 30, 40, 50, 75, 100, 150, 200, 300, 400, the SEQ ID NO: 1 as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. Particularly preferred polynucleotides are those which encode the epitopes as set forth in SEQ ID NOS: 13-94.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In certain preferred embodiments, the polynucleotides described above, e.g., polynucleotide variants, fragments and hybridizing sequences, encode polypeptides that are immunologically cross-reactive with a polypeptide sequence specifically set forth in SEQ ID NO:1 or SEQ ID NO:3. In other preferred embodiments, such polynucleotides encode polypeptides that have a level of immunogenic activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403410, respectively. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=-4 and a comparison of both strands.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Therefore, in another embodiment of the invention, a mutagenesis approach, such as site-specific mutagenesis, is employed for the preparation of immunogenic variants and/or derivatives of the polypeptides described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the immunogenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants of the present invention, recursive sequence recombination, as described in U.S. Pat. No. 5,837,458, may be employed. In this approach, iterative cycles of recombination and screening or selection are performed to "evolve" individual polynucleotide variants of the invention having, for example, enhanced immunogenic activity.

According to another embodiment of the present invention, polynucleotide compositions comprising antisense oligonucleotides are provided. Antisense oligonucleotides have been demonstrated to be effective and targeted inhibitors of protein synthesis, and, consequently, provide a therapeutic approach by which a disease can be treated by inhibiting the synthesis of proteins that contribute to the disease. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829). Further, examples of antisense inhibition have been demonstrated with the nuclear protein cyclin, the multiple drug resistance gene (MDG1), ICAM-1, E-selectin, STK-1, striatal GABAA receptor and human EGF (Jaskulski et al., Science. 1988 June 10;240(4858): 1544-6; Vasanthakumar and Ahmed, Cancer Commun. 1989; 1(4): 225-32; Peris et al., Brain Res Mol Brain Res. 1998 June 15;57(2):310-20; U.S. Pat. No. 5,801,154; U.S. Pat. No. 5,789,573; U.S. Pat. No. 5,718,709 and U.S. Pat. No. 5,610, 288). Antisense constructs have also been described that inhibit and can be used to treat a variety of abnormal cellular proliferations, e.g. cancer (U.S. Pat. No. 5,747,470; U.S. Pat. No. 5,591,317 and U.S. Pat. No. 5,783,683).

Therefore, in certain embodiments, the present invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein.

Selection of antisense compositions specific for a given gene sequence is based upon analysis of the chosen target sequence (i.e. in these illustrative examples the rat and human sequences) and determination of secondary structure, Tm, binding energy, relative stability, and antisense compositions were selected based upon their relative inability to form dimers, hairpins, or other secondary structures that would reduce or prohibit specific binding to the target mRNA in a host cell.

Highly preferred target regions of the mRNA, are those which are at or near the AUG translation initiation codon, and those sequences which are substantially complementary to 5' regions of the mRNA. These secondary structure analyses and target site selection considerations can be performed, for example, using v.4 of the OLIGO primer analysis software and/or the BLASTN 2.0.5 algorithm software (Altschul et al., Nucleic Acids Res. 1997 September 1;25(17):3389-402).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., Nucleic Acids Res. 1997 July 15;25(14):2730-6). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane.

According to another embodiment of the invention, the polynucleotide compositions described herein are used in the design and preparation of ribozyme molecules for inhibiting expression of the tumor polypeptides and proteins of the present invention in tumor cells. Ribozymes are RNA-protein complexes that cleave nucleic acids in a site-specific fashion. Ribozymes have specific catalytic domains that possess endonuclease activity (Kim and Cech, Proc Natl Acad Sci USA. 1987 December;84(24):8788-92; Forster and Symons, Cell. 1987 April 24;49(2):211-20). For example, a large number of ribozymes accelerate phosphoester transfer reactions with a high degree of specificity, often cleaving only one of several phosphoesters in an oligonucleotide substrate (Cech et al., Cell. 1981 December; 27(3 Pt 2):487-96; Michel and Westhof, J Mol. Biol. 1990 December 5;216(3):585-610; Reinhold-Hurek and Shub, Nature. 1992May 14;357(6374): 173-6). This specificity has been attributed to the requirement that the substrate bind via specific base-pairing interactions to the internal guide sequence ("IGS") of the ribozyme prior to chemical reaction.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., Proc Natl Acad Sci USA. 1992 August 15;89 (16):7305-9). Thus, the specificity of action of a ribozyme is greater than that of an antisense oligonucleotide binding the same RNA site.

The enzymatic nucleic acid molecule may be formed in a hammerhead, hairpin, a hepatitis 67 virus, group I intron or RNaseP RNA (in association with an RNA guide sequence) or Neurospora VS RNA motif. Examples of hammerhead motifs are described by Rossi et al. Nucleic Acids Res. 1992 September 11;20(17):4559-65. Examples of hairpin motifs are described by Hampel et al. (Eur. Pat. Appl. Publ. No. EP 0360257), Hampel and Tritz, Biochemistry 1989 June 13;28 (12):4929-33; Hampel et al., Nucleic Acids Res. 1990 January 25;18(2):299-304 and U.S. Pat. No. 5,631,359. An example of the hepatitis δ virus motif is described by Perrotta and Been, Biochemistry. 1992 December 1;31(47):11843-52; an example of the RNaseP motif is described by Guerrier-Takada et al., Cell. 1983 December;35(3 Pt 2):849-57; Neurospora VS RNA ribozyme motif is described by Collins (Saville and Collins, Cell. 1990 May 18;61(4):685-96; Saville and Collins, Proc Natl Acad Sci USA. 1991 October 1;88(19):8826-30; Collins and Olive, Biochemistry. 1993 March 23;32(11):2795-9); and an example of the Group I intron is described in (U.S. Pat. No. 4,987,071). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery.

More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol III or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells Ribozymes expressed from such promoters have been shown to function in mammalian cells. Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

In another embodiment of the invention, peptide nucleic acids (PNAs) compositions are provided. PNA is a DNA mimic in which the nucleobases are attached to a pseudopeptide backbone (Good and Nielsen, Antisense Nucleic Acid Drug Dev. 1997 7(4) 431-37). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (*Trends Biotechnol* 1997 June;15(6): 224-9). As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., *Science* 1991 December 6;254(5037):1497-500; Hanvey et al., Science. 1992 November 27;258(5087):1481-5; Hyrup and Nielsen, Bioorg Med Chem. 1996 January;4(1):5-23). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc or Fmoc protocols for solid-phase peptide synthesis, although other methods, including a modified Merrifield method, have been used.

PNA monomers or ready-made oligomers are commercially available from PerSeptive Biosystems (Framingham, Mass.). PNA syntheses by either Boc or Fmoc protocols are straightforward using manual or automated protocols (Norton et al., Bioorg Med Chem. 1995 April;3(4):437-45). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography, providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (for example, Norton et al., Bioorg Med Chem. 1995 April;3(4):437-45; Petersen et al., J Pept Sci. 1995 May-June;1(3):175-83; Orum et al., Biotechniques. 1995 September;19(3):472-80; Footer et al., Biochemistry. 1996 August 20;35(33):10673-9; Griffith et al., Nucleic Acids Res. 1995 August 11;23(15):3003-8; Pardridge et al., Proc Natl Acad Sci USA. 1995 June 6;92(12):5592-6; Boffa et al., Proc Natl Acad Sci USA. 1995 March 14;92(6):1901-5; Gambacorti-Passerini et al., Blood. 1996 August 15;88(4): 1411-7; Armitage et al., Proc Natl Acad Sci USA. 1997 November 11;94(23):12320-5; Seeger et al., Biotechniques. 1997 September;23(3):512-7). U.S. Pat. No. 5,700,922 discusses PNA-DNA-PNA chimeric molecules and their uses in diagnostics, modulating protein in organisms, and treatment of conditions susceptible to therapeutics.

Methods of characterizing the antisense binding properties of PNAs are discussed in Rose (Anal Chem. 1993 December 15;65(24):3545-9) and Jensen et al. (Biochemistry. 1997 April 22;36(16):5072-7). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs that have been described and will be apparent to the skilled artisan include use in DNA strand invasion, antisense inhibition, mutational analysis, enhancers of transcription, nucleic acid purification, isolation of transcriptionally active genes, blocking of transcription factor binding, genome cleavage, biosensors, in situ hybridization, and the like.

Polynucleotide Characterization and Expression

Polynucleotides compositions of the present invention may be prepared and/or manipulated using any of a variety of well established techniques (see generally, Sambrook et al., *Molecular Cloning: A Laboratory Manual,* Cold Spring Harbor Laboratories, Cold Spring Harbor, N.Y., 1989, and other like references).

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215-223, Horn, T. et al. (1980) *Nucl. Acids Res. Symp. Ser.* 225-232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202-204) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, W H Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, any of a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem.* 264:5503-5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) *Methods Enzymol.* 153:516-544.

In cases where plant expression vectors are used, the expression of sequences encoding polypeptides may be driven by any of a number of promoters. For example, viral promoters such as the $^{35}$S and 19S promoters of CaMV may be used alone or in combination with the omega leader sequence from TMV (Takamatsu, N. (1987) *EMBO J.* 6:307-

311. Alternatively, plant promoters such as the small subunit of RUBISCO or heat shock promoters may be used (Coruzzi, G. et al. (1984) *EMBO J.* 3:1671-1680; Broglie, R. et al. (1984) *Science* 224:838-843; and Winter, J. et al. (1991) *Results Probl. Cell Differ.* 17:85-105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191-196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia larvae.* The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard, E. K. et al. (1994) *Proc. Natl. Acad. Sci.* 91 :3224-3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, COS, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223-32) and adenine phosphoribosyltransferase (Lowy, I. et al. (1990) *Cell* 22:817-23) genes which can be employed in tk.sup.- or aprt.sup.- cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567-70); npt, which confers resistance to the aminoglycosides, neomycin and G-418 (Colbere-Garapin, F. et al (1981) *J. Mol. Biol.* 150:1-14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121-131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992*, Prot. Exp. Purif.* 3:263-281) while the enterokinase cleavage site provides a means for purifying the desired polypeptide from the fusion protein. A discussion of vectors which contain fusion proteins is provided in Kroll, D. J. et al. (1993*; DNA Cell Biol.* 12:441-453).

In addition to recombinant production methods, polypeptides of the invention, and fragments thereof, may be produced by direct peptide synthesis using solid-phase techniques (Merrifield J. (1963) *J. Am. Chem. Soc.* 85:2149-2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

T Cells Compositions

The present invention, in another aspect, provides T cells specific for a tumor polypeptide disclosed herein, or for a variant or derivative thereof. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a polypeptide, polynucleotide encoding a polypeptide and/or an antigen presenting cell (APC) that expresses such a polypeptide. Such stimulation is performed under conditions and for a time sufficient to permit the generation of T cells that are specific for the polypeptide of interest. Preferably, a tumor polypeptide or polynucleotide of the invention is present within a delivery vehicle, such as a microsphere, to facilitate the generation of specific T cells.

T cells are considered to be specific for a polypeptide of the present invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065-1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a tumor polypeptide (100 ng/ml-100 μg/ml, preferably 200 ng/ml-25 μg/ml) for 3-7 days will typically result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a tumor polypeptide, polynucleotide or polypeptide-expressing APC may be $CD4^+$ and/or $CD8^+$. Tumor polypeptide-specific T cells may be expanded using standard techniques. Within preferred embodiments, the T cells are derived from a patient, a related donor or an unrelated donor, and are administered to the patient following stimulation and expansion.

For therapeutic purposes, $CD4^+$ or $CD8^+$ T cells that proliferate in response to a tumor polypeptide, polynucleotide or APC can be expanded in number either in vitro or in vivo. Proliferation of such T cells in vitro may be accomplished in a variety of ways. For example, the T cells can be re-exposed to a tumor polypeptide, or a short peptide corresponding to an immunogenic portion of such a polypeptide, with or without the addition of T cell growth factors, such as interleukin-2, and/or stimulator cells that synthesize a tumor polypeptide. Alternatively, one or more T cells that proliferate in the presence of the tumor polypeptide can be expanded in number by cloning. Methods for cloning cells are well known in the art, and include limiting dilution.

Pharmaceutical Compositions

In additional embodiments, the present invention concerns formulation of one or more of the polynucleotide, polypeptide or T-cell disclosed herein in pharmaceutically-acceptable solutions for administration to a cell or an animal, either alone, or in combination with one or more other modalities of therapy. In particular, the present invention concerns, the use of cripto polynucleotides, polypeptides, fragments, fusions and variants in a pharmaceutical composition for the treatment of tumours. In particular it is preferred that the Cripto is Cripto 1.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Therefore, in another aspect of the present invention, pharmaceutical compositions are provided comprising one or more of the polynucleotide, polypeptide and/or T-cell compositions described herein in combination with a physiologically acceptable carrier. In certain preferred embodiments, the pharmaceutical compositions of the invention comprise immunogenic polynucleotide and/or polypeptide compositions of the invention for use in prophylactic and theraputic vaccine applications. Vaccine preparation is generally described in, for example, M. F. Powell and M. J. Newman, eds., "Vaccine Design (the subunit and adjuvant approach)," Plenum Press (NY, 1995). Generally, such compositions will comprise one or more polynucleotide and/or polypeptide compositions of the present invention in combination with one or more immunostimulants.

It will be apparent that any of the pharmaceutical compositions described herein can contain pharmaceutically acceptable salts of the polynucleotides and polypeptides of the invention. Such salts can be prepared, for example, from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

In another embodiment, illustrative immunogenic compositions, e.g., vaccine compositions, of the present invention comprise DNA encoding one or more of the polypeptides as described above, such that the polypeptide is generated in situ. As noted above, the polynucleotide may be administered within any of a variety of delivery systems known to those of ordinary skill in the art. Indeed, numerous gene delivery techniques are well known in the art, such as those described by Rolland, *Crit. Rev. Therap. Drug Canier Systems* 15:143-198, 1998, and references cited therein. Appropriate polynucleotide expression systems will, of course, contain the necessary regulatory DNA regulatory sequences for expression in a patient (such as a suitable promoter and terminating signal). Alternatively, bacterial delivery systems may involve the administration of a bacterium (such as Bacillus-Calnette-Guerrin) that expresses an immunogenic portion of the polypeptide on its cell surface or secretes such an epitope.

Therefore, in certain embodiments, polynucleotides encoding immunogenic polypeptides described herein are introduced into suitable mammalian host cells for expression using any of a number of known viral-based systems. In one illustrative embodiment, retroviruses provide a convenient and effective platform for gene delivery systems. A selected nucleotide sequence encoding a polypeptide of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) J. Virol. 57:267-274; Bett et al. (1993) J. Virol. 67:5911-5921; Mittereder et al. (1994) Human Gene Therapy 5:717-729; Seth et al. (1994) J. Virol. 68:933-940; Barr et al. (1994) Gene Therapy 1:51-58; Berkner, K. L. (1988) BioTechniques 6:616-629; and Rich et al. (1993) Human Gene Therapy 4:461-476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179:1867-1875.

Additional viral vectors useful for delivering the nucleic acid molecules encoding polypeptides of the present invention by gene transfer include those derived from the pox family of viruses, such as vaccinia virus and avian poxvirus. By way of example, vaccinia virus recombinants expressing the novel molecules can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the polypeptide of interest into the viral genome. The resulting TK.sup.(−) recombinant can be selected by culturing the cells in the presence of 5-bromodeoxyuridine and picking viral plaques resistant thereto.

A vaccinia-based infection/transfection system can be conveniently used to provide for inducible, transient expression or coexpression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al. Proc. Natl. Acad. Sci. USA (1986) 83:8122-8126.

Alternatively, avipoxviruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions of the present invention, such as those vectors described in U.S. Pat. Nos. 5,843, 723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. J. Biol. Chem. (1993) 268:6866-6869 and Wagner et al. Proc. Natl. Acad. Sci. USA (1992) 89:6099-6103, can also be used for gene delivery under the invention.

Additional illustrative information on these and other known viral-based delivery systems can be found, for example, in Fisher-Hoch et al., *Proc. Natl. Acad. Sci. USA* 86:317-321, 1989; Flexner et al., *Ann. N.Y. Acad. Sci.* 569: 86-103, 1989; Flexner et al., *Vaccine* 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627, 1988; Rosenfeld et al., *Science* 252:431-434, 1991; Kolls et al., *Proc. Natl. Acad. Sci. USA* 91:215-219, 1994; Kass-Eisler et al., *Proc. Natl. Acad. Sci. USA* 90:11498-11502, 1993; Guzman et al., *Circulation* 88:2838-2848, 1993; and Guzman et al., *Cir. Res.* 73:1202-1207, 1993.

In another embodiment of the invention, a polynucleotide is administered/delivered as "naked" DNA, for example as described in Ulmer et al., *Science* 259:1745-1749, 1993 and reviewed by Cohen, *Science* 259:1691-1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest. The particles, when delivering nucleic acid are preferably gold beads of a 0.4-4.0 um, more preferably 0.6-2.0 um diameter and the DNA conjugate coated onto these and then encased in a cartridge for placing into the "gene gun". The particles are typically and preferably delivered to the skin. Other means of delivery to the skin, comprise utilising needle delivery via a needle of a liquid formulation.

DNA vaccines usually consist of a bacterial plasmid vector into which is inserted a strong, normally viral, promoter, the gene of interest which encodes for an antigenic peptide and a polyadenylation/transcriptional termination sequences. Thus gene of interest may encode a full cripto protein as described or simply an antigenic peptide sequence such as described in seq ID no 13-94. The plasmid can be grown in bacteria, such as for example *E. coli* and then isolated and prepared in an appropriate medium, depending upon the intended route of administration, before being administered to the host. Following administration the plasmid is taken up by cells of the host where the encoded peptide is produced. The plasmid vector will preferably be made without an origin of replication which is functional in eukaryotic cells, in order to prevent plasmid replication in the mammalian host and integration within chromosomal DNA of the animal concerned.

There are a number of advantages of DNA vaccination relative to traditional vaccination techniques. First, it is predicted that because of the proteins which are encoded by the DNA sequence are synthesised in the host, the structure or conformation of the protein will be similar to the native protein associated with the disease state. It is also likely that DNA vaccination will offer protection against different strains of a virus, by generating cytotoxic T lymphocyte response that recognise epitopes from conserved proteins. Furthermore, because the plasmids are taken up by the host cells where antigenic protein can be produced, a long-lasting immune response will be elicited. The technology also offers the possibility of combing diverse immunogens/epitopes into a single preparation.

Helpful background information in relation to DNA vaccination is provided in Donnelly et al "DNA vaccines" Ann. Rev Immunol. 1997 15: 617-648, the disclosure of which is included herein in its entirety by way of reference.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

According to another embodiment, the pharmaceutical compositions described herein will comprise one or more immunostimulants in addition to the immunogenic polynucleotide, polypeptide, T-cell and/or APC compositions of this invention. An immunostimulant refers to essentially any substance that enhances or potentiates an immune response (antibody and/or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, *Bordatella peitussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Within certain embodiments of the invention, the adjuvant composition is preferably one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Anti. Rev. Immunol.* 7:145-173, 1989.

Certain preferred adjuvants for eliciting a predominantly Th1-type response include, for example, a combination of monophosphoryl lipid A, preferably 3-de-O-acylated monophosphoryl lipid A, together with an aluminum salt. MPL® adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., Science 273:352, 1996. Another preferred adjuvant comprises a saponin, such as Quil A, or derivatives thereof, including QS21 and QS7 (Aquila Biopharmaceuticals Inc., Framingham, Mass.); Escin; Digitonin; or Gypsophila or *Chenopodium quinoa* saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol$^R$ to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 as disclosed in WO 00/09159. Preferably the formulation additionally comprises an oil in water emulsion and tocopherol.

Additional illustrative adjuvants for use in the pharmaceutical compositions of the invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Enhanzyn®) (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Other preferred adjuvants include adjuvant molecules of the general formula (I):

$$HO(CH_2CH_2O)_n\text{-}A\text{-}R$$

Wherein, n is 1-50, A is a bond or —C(O)—, R is $C_{1-50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4-24, most preferably 9; the R component is $C_{1-50}$, preferably $C_4$-$C_{20}$ alkyl and most preferably $C_{12}$ alkyl, and A is a bond. The concentration of the polyoxyethylene ethers should be in the range 0.1-20%, preferably from 0.1-10%, and most preferably in the range 0.1-1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index (12$^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

According to another embodiment of this invention, an immunogenic composition described herein is delivered to a host via antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245-251, 1998) and have been shown to be effective as a physiological adjuvant for eliciting prophylactic or therapeutic antitumor immunity (see Timmerman and Levy, *Ann. Rev. Med.* 50:507-529, 1999). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594-600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide of the invention (or portion or other variant thereof) such that the encoded polypeptide, or an immunogenic portion thereof, is expressed on the cell surface. Such transfection may take place ex vivo, and a pharmaceutical composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456460, 1997. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems, such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature 1997 March 27;386(6623):410-4; Hwang et al., Crit Rev Ther Drug Carrier Syst 1998;15(3):243-84; U.S. Pat. No. 5,641,515; U.S. Pat. No. 5,580,579 and U.S. Pat. No. 5,792,451). Tablets, troches, pills, capsules and the like may also contain any of a variety of additional components, for example, a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Of course, any material used in preparing any dosage unit form should be pharmaceutically pure and substantially non-toxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally or intradermally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. No. 5,756,353 and U.S. Pat. No. 5,804,212. Likewise, the delivery of drugs using intranasal microparticle resins (Takenaga et al., J Controlled Release 1998 March 2;52(1-2):81-7) and lysophosphatidyl-glycerol compounds (U.S. Pat. No. 5,725,871) are also well-known in the pharmaceutical arts.

Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol 1998 July;16(7):307-21; Takakura, Nippon Rinsho 1998 March;56(3):691-5; Chandran et al., Indian J Exp Biol. 1997August;35(8):801-9; Margalit, Crit Rev Ther Drug Carrier Syst. 1995;12(2-3):233-61; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Remeisen et al., J Biol. Chem. 1990 September 25;265(27):1633742; Muller et al., DNA Cell Biol. 1990 April 9(3):221-9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, he use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 December;24(12):1113-28). To avoid side effects due to intracellular polymeric overloading, such ultrafine particles (sized around 0.1 μm) may be designed using polymers able to be degraded in vivo. Such particles can be made as described, for example, by Couvreur et al., Crit Rev Ther Drug Carrier Syst. 1988;5(1):1-20; zur Muhlen et al., Eur J Pharm Biopharm. 1998 March;45(2): 149-55; Zambaux et al. J Controlled Release. 1998 January 2 50(1-3):3140; and U.S. Pat. No. 5,145,684.

Cancer Therapeutic Methods

In further aspects of the present invention, the pharmaceutical compositions described herein may be used for the treatment of cancer, particularly for the immunotherapy of colon or colorectal cancer. In other embodiments the compositions can be used to treat breast, or non-small cell lung carcinoma. Typically the composition will be useful for treating patients whose cancers express cripto antigen and/or whose metastases express cripto antigen. Within such methods, the pharmaceutical compositions described herein are administered to a patient, typically a warm-blooded animal, preferably a human. A patient may or may not be afflicted with cancer. Accordingly, the above pharmaceutical compositions may be used to prevent the development of a cancer or to treat a patient afflicted with a cancer. Pharmaceutical compositions and vaccines may be administered either prior to or following surgical removal of primary tumors and/or treatment such as administration of radiotherapy or conventional chemotherapeutic drugs. As discussed above, administration of the pharmaceutical compositions may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells) that can directly or indirectly mediate antitumor effects and does not necessarily depend on an intact host immune system. Examples of effector cells include T cells as discussed above, T lymphocytes (such as CD8+ cytotoxic T lymphocytes and CD4+ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., Immunological Reviews 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous, intradermally or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10-50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 μg to 5 mg per kg of host. Suitable dose sizes will vary with the size of the patient, but will typically range from about 0.1 ml to about 5 ml.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

EXAMPLE 1a

Expression of Immunoreactive Cripto-1 in Human Lesions

| Tissue | Non-involved Epithelium | Premalignant Lesion | | Carcinoma |
|---|---|---|---|---|
| | | TA | TVA | |
| Colon | 25/193 (13) | 26/65(40) | 10/13 (77) | 122/168 (73)** |
| | | IM | | 17/37 (46)** |
| Stomach | 1/37 (3) | 16/30 (53) | | |
| Pancreas | 10/58 (17) | | | 58/98 (59)** |
| | | Hyperplasias | Adenomas | |
| Gall Bladder | N.D. | 6/9(67) | 4/7(58) | 89/132 (68)** |

-continued

| | | | | | |
|---|---|---|---|---|---|
| | | | | DCIS | |
| Breast | 5/33 (15) | | | 26/55 (47) | 497/631 (79)** |
| Non Small Cell Lung | | | | | 178/195 (91)** |

| Tissue | Non-involved Epithelium | Cystadenomas Serous | Mucinous | Serous | Mucinous |
|---|---|---|---|---|---|
| Ovary | 6/7 (86) post-menopausal | 6/14 (43) | 0/7 | 4/10 (40) | 4/5 (80) |
| | | | | | 23/40 (58) |
| | | | | | 25/48 (52) |
| | | 3/9 (33) | 3/8 (38) | 4/8 (50) | 9/10 (90) |
| | | | | Borderline: 10/10 | |
| Endo-metrium | 10/28 (36) post-menopausal | | | | 53/91 (58)* |
| | | | | Hyperplasias | |
| | | | | 18/30 (60) | 68/96 (71)* |
| Cervix | 4/25 (17) | | | | 40/74 (54)* |
| Testis | 0/3 | | | | 29/51 (57)** |
| | | | Embryonal Carcinomas | | Seminomas |
| | | | 19/19 (100)** | | 10/32 (31) |
| Adrenal Cortex | | | | | 1/3 (33) |
| Bladder | 0/6 | | | | 23/39 (60)** |
| Renal | | | | | 0/18 |
| Prostate | | | | | 0/9 |

TA = Tubular adenoma
TVC = Tubulovillous adenoma
IM = Intestinal metaplasia
**Statistically significant expresson in carcinomas over non-involved tissues

EXAMPLES

EXAMPLE 1.6

Over-Expression of Cripto in Cancerous Tissues

Real-time RT-PCR (U. Gibson. 1996. Genome Research: 6,996) is used to compare mRNA transcript abundance of the target protein in a panel of normal and tumor tissues and/or cell lines. This analysis is critical to establish the tumor specificity of Cripto expression, which is an important criterion a good vaccine candidate must fulfil.

Total RNA is extracted from snap frozen biopsies or cell lines using TriPure reagent (Roche). Total RNA from normal tissues is also purchased from InVitrogen. Poly-A+ mRNA is purified from total RNA after DNAase treatment using oligo-dT magnetic beads (Dynal). Quantification of the mRNA is performed by spectrofluorimetry (VersaFluor, BioRad) using RiboGreen dye (Molecular Probes).

TaqMan primers (forward primer sequence: TGGGTAGGAAAGAGGAAGCAAAT, SEQ ID NO:7; reverse primer sequence: TGCTTCTCTACCACCACCTAATCA, SEQ ID NO:8) and probe for real-time RT-PCR amplification are designed with the Perkin-Elmer Primer Express software using default options for TaqMan amplification conditions.

Real-time reactions are assembled according to standard PCR protocols using 2 ng of reverse transcribed mRNA (Expand RT, Roche) for each reaction. Either SybrI or TaqMan detection is undergone, depending on the evaluated sample.

In case of SybrI detection, SybrI dye (Molecular Probes) is added at a final dilution of 1/75000 for real-time detection, and TaqMan probe is omitted. Amplification (40 cycles) and real-time detection is performed in a Perkin-Elmer Biosystems PE7700 system using conventional instrument settings. Ct values are calculated using the PE7700 Sequence Detector Software. Ct values are obtained from each tissue sample for the target mRNA (CtX) and for the actin mRNA (CtA).

As the efficiency of PCR amplification under the prevailing experimental conditions is close to the theoretical amplification efficiency, $2^{(CtA-CtX)}$ value is an estimate of the relative target transcript level of the sample, standardized with respect to Actin transcript level. A value of 1 thus suggests the candidate antigen and Actin have the same expression level.

RT-PCR analysis, using SybrI detection, was performed on a set of colon tumor and matched normal colon from 6 different patients and 48 normal tissue samples. A TaqMan detection was run on a set of colon tumor and matched normal colon from 6 other patients (reactions were run in triplicates) and 48 normal tissue samples. Tested normal tissues (and the abbreviations used in graphics) are shown below:

- Adrenal gland (Ad_Gl)
- Aorta (Ao)
- Bladder (Bl)
- Bonne marrow Bo_Ma
- Brain (Bra, Bra1, Bra2, Bra3, Bra4, Bra5)
- Cervix (Ce)
- Colon (Co)
- Fallopian tube (Fa_Tu)
- Heart (He)
- Ileum (I1)
- Kidney (Ki)
- Liver (Li, Li1, Li2)
- Lung (Lu)
- Lymph node (Ly_No)
- Esophagus (Oe)
- Ovary (Ov)
- Pancreas (Pa, Panc1, Panc2)
- Parathyrois (Pa_Thy)
- Placenta (Pl)
- Prostate (Pr)
- Rectum (Re)
- Skin (Sk)
- Skeletal muscle (Sk_Mu)
- Small intestine (Sm_In)
- Spleen (Sp)
- Stomach (St)
- Testis (Te)
- Thyroid (Thyr, Thy, Thy1, Thy2)
- Thymus (Thym1,) Thym2
- Trachea (Tr, Tra)

Real-time RT-PCR reactions, using Sybri detection, were also performed on a set of 7 lung cell lines:

- CRL-5803 (Carcinoma, Non-Small Cell Lung Cancer, large cell, neuroendocrine, metastatic site: lymph node)
- CRL-5807 (Bronchioalveolar carcinoma, Non-Small Cell Lung Cancer)
- CRL-5810 (Adenocarcinoma, Non-Small Cell Lung Cancer)
- CRL-5815 (Carcinoid, lung bronchus)
- CRL-5865 (Adenocarcinoma, metastatic site: pleural effusion)
- CRL-9609 (Normal lung, bronchus, epithelial, virus transformed)
- HTB-177 (Carcinoma, large cell lung cancer, pleural effusion) and 2 colon cell lines:
- CRL-2159 (Carcinoma, Cecum, Dukes' B)
- CCL-250

Fresh biopsy normal lung tissues (Lu(ucl), Lu(IVG)) and a lung tumor tissue (LuTum) were also performed as control.

RT-PCR results on colorectal biopsies and normal tissues are shown in FIGS. 1, 2, 3 and 4, and in Table 1. RT-PCR results on cell lines are shown in FIG. 5.

TABLE 1

Cripto expression in colorectal tumors and normal tissues.

| | Sybr detection[1] | TaqMan detection[1] |
|---|---|---|
| | Colorectal tumor versus adjacent normal colon[2] | |
| Number of over-expressing patients | 5/6 | 5/6 |
| Average over-expression fold in over-expressing patients | 200 | 90 |
| Median over-expression fold (minimum-maximum) | 64 (22-724) | 20 (4-397) |
| | Colorectal tumor versus average normal tissues[2] | |
| Number of over-expressing patients | 5/6 | 4/6 |
| Average over-expression fold in over-expressing patients | 10 | 12 |
| Median over-expression fold (minimum-maximum) | 11 (3-22) | 7 (3-32) |
| Normal tissues with a high transcript level[3] (normal-to-tumor ratio) | Spleen (0.5) | Spleen (0.75), ovary (2)[4] |

[1]Transcript levels were calculated in colorectal tumors and a panel of normal tissues using 2 detection techniques: TaqMan and Sybr. Regarding Cripto, TaqMan detection involved 6 patients and measures were done in triplicates, whereas Sybr detection was undergone on 6 different patients.

[2]Transcript level in colorectal tumors was compared to both matched normal colon and average of normal tissue transcript levels.

[3]A normal tissue has a high transcript level when it is higher than one fifth of colorectal tumors transcript level.

[4]Ovary has not been evaluated in Cripto Sybr experiment.

Table 1, FIGS. 1, 2, 3 & 4 clearly show that Cripto, while being marginally expressed in normal adult tissues, is highly over-expressed in a majority of colorectal tumors, with an over-expression rate of more than ten fold. Moreover, FIG. 5 indicates Cripto is dramatically over-expressed in a lung tumor cell line (CRL-5815). Cripto tumor associated antigen is therefore a suitable vaccine candidate to treat both colorectal and lung cancer patients.

EXAMPLE 2

Cloning of Cripto-1 c-DNA from Lung Tumor Cell Lines

Total RNA was extracted using TriPure reagent from $10^7$ cultured cells of 7 different lung cell lines (see section 1 for the complete list of cell lines). Total RNAs were pooled, and mRNA was purified from pooled total RNA on oligo-d(T) magnetic beads (Dynal). 250 ng of mRNA were used for cDNA synthesis. Quantification of the mRNA is performed by spectrofluorimetry (VersaFluor, BioRad) using RiboGreen dye (Molecular Probes). cDNA was synthesized using the GeneRacer technology (Invitrogen) which ensures the amplification of only full-length transcripts. mRNA was treated with CIP. mRNA 5' ends were decapped with TAP (Tobacco Acid Pyrophosphatase) and were ligated to a specific RNA oligonucleotide. The ligated mRNA was reverse transcribed into cDNA using an oligod(T)-tailed primer. Amplification of cDNA was performed using both GeneRacer flanking primers (Advantage, Clontech). Cripto amplification was performed on 10 ng of GeneRacer cDNA using gene specific PCR primers (forward primer sequence: CGTCCAAGGCCGAAAGCCCTCCAGTT, SEQ ID NO:9; and reverse primer sequence: TTGGGAGAGGGCAGGGCAAAGAAGTAAGAA, SEQ ID NO:10). PCR reaction was done with Advantage II Taq DNA polymerase (Clontech) under standard conditions. PCR product was cloned in pCR4-TOPO plasmid (Invitrogen). Amplified sequence (SEQ ID NO:95) was shown to display a variation at codon 22 (SEQ ID NO:96): Ala (GCC) instead of Val (GTC) in the native version (SeqID6). Native version was restored by PCR mutagenesis.

EXAMPLE 3

Immunogenicity of Cripto Tumor-Associated Antigen in Animal Models

The immunogenicity of the antigen of the present invention can be verified by immunizing rabbits and mice using various means of immunization. Indeed, immunization with Cripto forms, either peptide or recombinant protein could induce humoral immune response with the generation of specific antibodies against Cripto and/or could induce a Cripto specific cellular immune response. In vivo delivery of Cripto protein using for instance, naked DNA in an appropriate vector encoding Cripto or fragments of Cripto, Cripto genes delivered by a viral vector encoding Cripto or fragments of Critpo, could also be useful to demonstrate Cripto immunogenicity.

3.1: Synthetic Peptide Immunization.

The synthetic peptides from human Cripto-1 amino-acid sequence selected to immunize rabbits are GHQEFARPSRGYL (13 amino acids, SEQ ID NO:11), and QEEPAIRPRSSQRVPPMG (18 amino acids, SEQ ID NO:12). Synthetic peptides are then conjugated to a carrier protein (KLH). Conjugates are formulated with Freund's adjuvant, and two rabbits are immunized with each of the conjugates. Four weeks after the second immunization and four weeks after the third immunization, a blood sample is taken. Anti-Cripto antibody titers are estimated in the serum by ELISA and/or Western Blot following standard protocols (see section 3.5).

3.2: Nucleic Acids Immunization.

pcDNA3.1 vector (Invitrogen) is used to construct the vaccinating plasmid. To promote secretion of the in vivo translated protein and to therefore induce the humoral response against the present invention antigen, nucleic acid sequence encoding Cripto-1 with its own signal peptide is inserted into the vector polycloning site. The recombinant expression plasmid is used to transform a host *E. coli* strain such as BL21.

The above recombinant strain is grown in conventional cell culture medium. Bacteria are harvested before reaching the stationary phase. Plasmid preparation using Quiagen system is undergone for injection in mice.

Six to eight weeks-old Balb/c mice receive intramuscular injections of recombinant expression plasmid. Two weeks after the last injection, a blood sample is taken. Titers of specific antibodies elicited against the present invention antigen are determined by ELISA and/or Western Blot (see section 3.5).

3.3 Viral Vector Immunization Using Adenoviruses.

Recombinant adenoviruses are effective vectors for gene-based vaccination because they are capable of eliciting humoral and cellular immune responses against the encoded antigen. The nucleotide sequence coding for Cripto-1 protein with its own signal sequence could be inserted in an appropriated Adeno derivative viral vector. The adenoviral recombinant vector could be administrated to mice by different routes (intramuscular, intranasal, intradermal, subcutaneous or intraeperitoneal) After two week, blood samples could be taken and the titer of antibodies elicited examined. Additional experiments to measure the cellular immune response could also be performed.

3.4: Recombinant Protein Immunization.

3.4.1: Expression and Purification of Cripto-1 Recombinant Protein

Expression in microbial hosts, is used to produce the whole protein or fragments of the invention antigen for immunization purposes. Recombinant proteins may be expressed in two microbial hosts, *E. coli* and in yeast (such as *Saccharomyces cerevisiae* or *Pichia pastoris*). This allows the selection of the expression system with the best features for this particular antigen production.

The expression strategy first involves the design of the primary structure of the recombinant antigen. In general, an expression fusion partner (EFP) to improve levels of expression and/or an immune fusion partner (IFP) to modulate the immunogenic properties of the antigen, are placed at the N-terminal extremity. In addition, an affinity fusion partner (AFP) useful for facilitating further purification is included at the C-terminal end.

When the recombinant strains are available, the recombinant product is characterized by the evaluation of the level of expression and the prediction of further solubility of the engineered protein by analysis of its behavior in the crude extract.

After growth in appropriate culture medium and induction of the recombinant protein expression, total extracts are analyzed by SDS-PAGE. The recombinant proteins are visualized in stained gels and identified by Western blot analysis using the specific anti-peptide antibodies generated by peptide immunization in rabbit (see section 3.1).

A comparative evaluation of the different versions of the expressed antigen and expression hosts will allow the selection of the most promising candidate and host that is to be used for further purification and further immunological evaluation.

The purification schemes follow a classical approach based on the presence of a Histidine affinity tail in the recombinant protein. In a typical experiment the disrupted cells are filtered and the acellular extracts loaded onto an Ion Metal Affinity Chromatography (IMAC; Ni++NTA from Qiagen) that will specifically retain the recombinant protein. The retained proteins are eluted by 0-500 mM Imidazole gradient (possibly in presence of a detergent) in a phosphate buffer.

3.4.2: Protein immunization

Rabbits are immunized, intramuscularly several times at several week intervals with recombinant purified protein, formulated in the adjuvant 3D-MPL/QS21. Three weeks after each immunization, blood samples are taken. Anti-Cripto antibody titer is estimated in the serum by ELISA. The specificity of the anti-Cripto antibodies generated is tested by Western Blot (see section 3.5) using the purified protein and including appropriated controls.

3.5: Immunological Response Assays of Cripto-Immunized Animals.

Humoral response to Cripto immunization is assessed by measuring Cripto specific antibody titers in animal sera using ELISA and Western Blot. The following material harboring Cripto-1 derived peptides or full protein could be used for such test:

- Cripto synthetic peptides (see section 3.1 for possible peptides), or
- protein extracts from cultures of Cripto-expressing cell lines (see section 1 for possible cell lines), or
- lysates of COS cells that have been engineered to transiently express a Cripto recombinant plasmid (see below), or
- protein extracts of recombinant *E. coli* or yeast strains (see section 3.3.1 for recombinant strain generation), or
- purified recombinant antigen (see section 3.3.1 for antigen purification).

Transient expression of Cripto in COS cells is obtained by transiently transfecting COS cells with recombinant pcDNA3.1 plasmid prepared for nucleic acid vaccination (see section 3.2).

For ELISA reactions, one of the above mentioned antigen is coated on microtiter plates (purified recombinant protein is preferred). ELISA is then performed using standard protocol.

Western Blots are realized under standard conditions with one of the above mentioned antigen (purified recombinant protein is preferred, synthetic peptides are not used)

The cellular response can also be assessed by stimulating in vitro vaccinated mouse spleen cells with the peptides used to immunize the mice, or with antigen-derived overlapping peptides covering the whole antigen sequence.

EXAMPLE 4

Demonstration of Existing Cripto Specific Human T-Cell by In Vitro Priming

Immunological relevance of Cripto-1 can be further confirmed by in vitro priming of human T cells. All T cell lymphocytes, T cell lines and dendritic cells are derived from PBMCs (peripheral blood mononuclear cells) of healthy donors or cancer patients (preferred donors are from HLA-A2 subtype).

Epitopes Binding of HLA Alleles Prediction:

The HLA Class I binding peptide sequences (nonamers, decamers) are predicted either by the Parker's algorithm [Parker K, et al. 1994] (available on the world wide web at tbimas.dcrt.nih.gov/molibio/hla bind/) and the Rammensee method [Rammensee, et al. 1997] [Rammensee, et al. 1995] (available on the world wide web at syfpeithi.bmi-h-eldelberg.com/Scripts/MHCServer.dll/EpPredict.htm).

The HLA Class II binding peptide sequences (nonamers) are predicted using the Tepitope algorithm [Sturniolo, et al. 1999].

CD8+ T-Cell Response:

Two strategies to raise the CD8+ T cell lines are used: a peptide-based approach and a whole gene-based approach. Both approaches require the full-length cDNA of interest in the correct reading frame to be cloned in an appropriate delivery system and to be used to predict the sequence of the HLA binding peptides.

Peptide-Based Approach:

For this approach, an HLA-A2.1/Kb transgenic mouse model is used for screening of the HLA-A2.1 peptides. Briefly, transgenic mice are immunized with adjuvanted HLA-A2 peptides, those able to induce a CD8 response (as defined by an efficient lysis or g-IFN production on peptide-pulsed target cells) are further analyzed in the human system.

Human dendritic cells (cultured according to [Romani et al.]) will be pulsed with the selected peptides and used to stimulate CD8+-sorted T cells (by Facs). After several weekly stimulation, the CD8+lines are first tested on peptide-pulsed autologous BLCL (EBV-B transformed cell lines). To verify the proper in vivo processing of the peptide, the CD8+ lines are then tested on cDNA-transfected tumor cells (HLA-A2 transfected LnCaP, Skov3 or CAMA tumor cells).

Whole Gene-Based Approach:

CD8+ T cell lines are primed and stimulated with either gene-gun transfected dendritic cells, retrovirally transduced B7.1-transfected fibroblasts, recombinant pox virus [Kim et al.] or adenovirus [Butterfield et al.] infected dendritic cells. Virus infected cells are very efficient to present antigenic peptides since the antigen is expressed at high level but can only be used once to avoid the over-growth of viral T cells lines.

After alternated stimulation, the CD8+ lines are tested on cDNA-transfected tumor cells as indicated above. Peptide specificity and identity is determined to confirm the immunological validation of antigen of the present invention.

CD4+ T-Cell Response:

Similarly, the CD4+ T-cell immune response can also be assessed. Generation of specific CD4+ T cells is made using dendritic cells loaded with recombinant purified protein or peptides to stimulate the T-cells.

Results:

A—Prediction of Class I Epitopes Using the Parker Method.

A-1 Cripto-1 and -3 Class I Epitopes.

| HLA allele | Epitope size | Start position | Sequence | Score | SEQ ID NO: |
|---|---|---|---|---|---|
| A68 | Decamer | 12 | SVIWIMAISK | 240.000 | SEQ ID NO:13 |
| A68 | Decamer | 117 | SVPHDTWLPK | 120.000 | SEQ ID NO:14 |
| B2705 | Nonamer | 33 | HQEFARPSR | 100.000 | SEQ ID NO:15 |
| B2705 | Nonamer | 59 | IRPRSSQRV | 600.000 | SEQ ID NO:16 |
| B2705 | Nonamer | 72 | IQHSKELNR | 100.000 | SEQ ID NO:17 |
| B2705 | Nonamer | 103 | GRNCEHDVR | 1000.000 | SEQ ID NO:18 |
| B2705 | Nonamer | 110 | VRKENCGSV | 600.000 | SEQ ID NO:19 |
| B2705 | Nonamer | 138 | LRCFPQAFL | 2000.000 | SEQ ID NO:20 |
| B2705 | Nonamer | 161 | SRTPELPPS | 200.000 | SEQ ID NO:21 |
| B2705 | Decamer | 65 | QRVPPMGIQH | 200.000 | SEQ ID NO:22 |
| B2705 | Decamer | 79 | NRTCCLNGGT | 200.000 | SEQ ID NO:23 |
| B2705 | Decamer | 103 | GRNCEHDVRK | 2000.000 | SEQ ID NO:93 |
| B2705 | Decamer | 136 | GQLRCFPQAF | 100.000 | SEQ ID NO:24 |
| B2705 | Decamer | 161 | SRTPELPPSA | 200.000 | SEQ ID NO:94 |
| B5101 | Decamer | 143 | QAFLPGCDGL | 110.000 | SEQ ID NO:25 |

-continued

| HLA allele | Epitope size | Start position | Sequence | Score | SEQ ID NO: |
|---|---|---|---|---|---|
| B5102 | Decamer | 143 | QAFLPGCDGL | 302.500 | SEQ ID NO:25 |
| B5102 | Decamer | 150 | DGLVMDEHLV | 120.000 | SEQ ID NO:26 |
| B60 | Nonamer | 23 | FELGLVAGL | 325.000 | SEQ ID NO:27 |
| B60 | Nonamer | 76 | KELNRTCCL | 320.000 | SEQ ID NO:28 |
| B62 | Nonamer | 137 | QLRCFPQAF | 240.000 | SEQ ID NO:29 |
| B62 | Decamer | 136 | GQLRCFPQAF | 160.000 | SEQ ID NO:24 |
| B7 | Nonamer | 169 | SARTTTFML | 120.000 | SEQ ID NO:30 |

A-2 Cripto-1 Specific Class I Epitopes.

| HLA allele | Epitope size | Start position | Sequence | Score | SEQ ID NO: |
|---|---|---|---|---|---|
| A0201 | Nonamer | 5 | KMARFSYSV | 668.086 | SEQ ID NO:31 |
| A0201 | Decamer | 16 | IMAISKVFEL | 349.885 | SEQ ID NO:32 |
| A0201 | Decamer | 13 | VIWIMAISKV | 310.361 | SEQ ID NO:33 |
| A0201 | Decamer | 175 | FMLVGICLSI | 128.242 | SEQ ID NO:34 |
| B2702 | Nonamer | 7 | ARFSYSVIW | 500.000 | SEQ ID NO:35 |
| B2702 | Nonamer | 3 | CRKMARFSY | 200.000 | SEQ ID NO:36 |
| B2702 | Decamer | 7 | ARFSYSVIWI | 300.000 | SEQ ID NO:37 |
| B2702 | Decamer | 37 | ARPSRGYLAF | 200.000 | SEQ ID NO:38 |
| B2705 | Nonamer | 7 | ARFSYSVIW | 1000.000 | SEQ ID NO:35 |
| B2705 | Nonamer | 3 | CRKMARFSY | 1000.000 | SEQ ID NO:36 |
| B2705 | Nonamer | 170 | ARTTTFMLV | 600.000 | SEQ ID NO:39 |
| B2705 | Nonamer | 37 | ARPSRGYLA | 200.000 | SEQ ID NO:40 |
| B2705 | Decamer | 7 | ARFSYSVIWI | 3000.000 | SEQ ID NO:37 |
| B2705 | Decamer | 37 | ARPSRGYLAF | 1000.000 | SEQ ID NO:38 |
| B2705 | Decamer | 3 | CRKMARFSYS | 200.000 | SEQ ID NO:41 |
| B4403 | Decamer | 34 | QEFARPSRGY | 120.000 | SEQ ID NO:42 |
| B5101 | Nonamer | 6 | MARFSYSVI | 286.000 | SEQ ID NO:43 |
| B5101 | Decamer | 169 | SARTTTFMLV | 110.000 | SEQ ID NO:44 |
| B5102 | Nonamer | 17 | MAISKVFEL | 150.000 | SEQ ID NO:45 |
| B5102 | Nonamer | 6 | MARFSYSVI | 100.000 | SEQ ID NO:43 |
| B5103 | Nonamer | 6 | MARFSYSVI | 100.000 | SEQ ID NO:43 |
| B5103 | Decamer | 169 | SARTTTFMLV | 121.000 | SEQ ID NO:44 |
| B7 | Nonamer | 36 | FARPSRGYL | 180.000 | SEQ ID NO:46 |

A-3 Cripto-3 Specific Class I Epitopes.

| HLA allele | Epitope size | Start position | Sequence | Score | SEQ ID NO: |
|---|---|---|---|---|---|
| A0201 | Nonamer | 5 | KMVRFSYSV | 668.086 | SEQ ID NO:47 |
| A0201 | Nonamer | 89 | CMLESFCAC | 103.417 | SEQ ID NO:48 |
| A0201 | Decamer | 16 | IMAISKAFEL | 152.124 | SEQ ID NO:49 |
| A0201 | Decamer | 175 | FMLAGICLSI | 128.242 | SEQ ID NO:50 |
| B2702 | Nonamer | 7 | VRFSYSVIW | 500.000 | SEQ ID NO:51 |
| B2702 | Nonamer | 3 | CRKMVRFSY | 200.000 | SEQ ID NO:52 |
| B2702 | Decamer | 7 | VRFSYSVIWI | 300.000 | SEQ ID NO:53 |
| B2702 | Decamer | 37 | ARPSRGDLAF | 200.000 | SEQ ID NO:54 |
| B2705 | Nonamer | 3 | CRKMVRFSY | 1000.000 | SEQ ID NO:52 |
| B2705 | Nonamer | 7 | VRFSYSVIW | 1000.000 | SEQ ID NO:51 |
| B2705 | Nonamer | 37 | ARPSRGDLA | 200.000 | SEQ ID NO:55 |
| B2705 | Nonamer | 170 | ARTTTFMLA | 200.000 | SEQ ID NO:56 |
| B2705 | Decamer | 7 | VRFSYSVIWI | 3000.000 | SEQ ID NO:53 |
| B2705 | Decamer | 37 | ARPSRGDLAF | 1000.000 | SEQ ID NO:54 |
| B2705 | Decamer | 59 | IRPRSSQRVL | 600.000 | SEQ ID NO:57 |
| B2705 | Decamer | 3 | CRKMVRFSYS | 200.000 | SEQ ID NO:58 |
| B2705 | Decamer | 65 | QRVLPMGIQH | 200.000 | SEQ ID NO:59 |
| B5101 | Nonamer | 60 | RPRSSQRVL | 120.000 | SEQ ID NO:60 |
| B5102 | Nonamer | 17 | MAISKAFEL | 150.000 | SEQ ID NO:61 |
| B7 | Nonamer | 60 | RPRSSQRVL | 800.000 | SEQ ID NO:60 |
| B7 | Nonamer | 36 | FARPSRGDL | 180.000 | SEQ ID NO:62 |

NB: Score is an estimate of half-time of disassociation of a molecule containing this subsequence.

B—Prediction of Class I Epitopes Using the Rammensee Method.

B-1 Cripto-1 and -3 Class I Epitopes.

| HLA allele | Epitope size | Start position | Sequence | Score | SEQ ID NO: |
|---|---|---|---|---|---|
| A26 | Nonamer | 179 | GICLSIQSY | 27 | SEQ ID NO:63 |
| A26 | Decamer | 27 | LVAGLGHQE F | 25 | SEQ ID NO:64 |
| A26 | Decamer | 121 | DTWLPKKCSL | 25 | SEQ ID NO:65 |
| A3 | Nonamer | 58 | AIRPRSSQR | 29 | SEQ ID NO:66 |
| A3 | Nonamer | 13 | VIWIMAISK | 24 | SEQ ID NO:67 |
| A3 | Decamer | 12 | SVIWIMAISK | 29 | SEQ ID NO:13 |
| A3 | Decamer | 117 | SVPHDTWLP K | 24 | SEQ ID NO:14 |
| B2705 | Nonamer | 103 | GRNCEHDVR | 25 | SEQ ID NO:18 |

-continued

| HLA allele | Epitope size | Start position | Sequence | Score | SEQ ID NO: |
|---|---|---|---|---|---|
| B2705 | Nonamer | 138 | LRCFPQAFL | 24 | SEQ ID NO:20 |

B-2 Cripto-1 Specific Class I Epitopes.

| HLA allele | Epitope size | Start position | Sequence | Score | SEQ ID NO: |
|---|---|---|---|---|---|
| A0201 | Nonamer | 83 | CLNGGTCML | 27 | SEQ ID NO:68 |
| A0201 | Nonamer | 5 | KMARFSYSV | 25 | SEQ ID NO:31 |
| A0201 | Decamer | 16 | IMAISKVFEL | 28 | SEQ ID NO:32 |
| A0201 | Decamer | 13 | VIWINAISKV | 26 | SEQ ID NO:33 |
| A26 | Nonamer | 35 | EFARPSRGY | 24 | SEQ ID NO:69 |
| A3 | Nonamer | 66 | RVPPMGIQH | 27 | SEQ ID NO:70 |
| A3 | Nonamer | 21 | KVFELGLVA | 24 | SEQ ID NO:71 |
| B08 | Nonamer | 17 | MAISKVFEL | 26 | SEQ ID NO:45 |
| B5101 | Nonamer | 6 | MARFSYSVI | 25 | SEQ ID NO:43 |

B-3 Cripto-3 Specific Class I Epitopes.

| HLA allele | Epitope size | Start position | Sequence | Score | SEQ ID NO: |
|---|---|---|---|---|---|
| A0201 | Nonamer | 83 | CLNGGTCML | 27 | SEQ ID NO:68 |
| A0201 | Nonamer | 176 | MLAGICLSI | 25 | SEQ ID NO:72 |
| A0201 | Decamer | 16 | IMAISKAFEL | 24 | SEQ ID NO:49 |
| A3 | Nonamer | 66 | RVLPMGIQH | 29 | SEQ ID NO:73 |
| B0702 | Nonamer | 60 | RPRSSQRVL | 24 | SEQ ID NO:60 |
| B08 | Nonamer | 17 | MAISKAFEL | 25 | SEQ ID NO:61 |

C—Prediction of Class II Epitopes Using the Tepitope Method.

C-1 Cripto-1 and -3 Class II Epitopes.

| HLA allele | Epitope size | Start position | Sequence | Score | SEQ ID NO: |
|---|---|---|---|---|---|
| DRB1*0102 | Nonamer | 70 | MGIQHSKEL | 1.8 | SEQ ID NO:74 |
| DRB1*0301 | Nonamer | 152 | LVMDEHLVA | 5.9 | SEQ ID NO:75 |
| DRB1*0301 | Nonamer | 158 | LVASRTPEL | 4.3 | SEQ ID NO:76 |
| DRB1*0401 | Nonamer | 152 | LVMDEHLVA | 3.2 | SEQ ID NO:75 |
| DRB1*0402 | Nonamer | 59 | IRPRSSQRV | 4.9 | SEQ ID NO:16 |

-continued

| HLA allele | Epitope size | Start position | Sequence | Score | SEQ ID NO: |
|---|---|---|---|---|---|
| DRB1*0703 | Nonamer | 11 | YSVIWIMAI | 6 | SEQ ID NO:77 |
| DRB1*0703 | Nonamer | 158 | LVASRTPEL | 5.7 | SEQ ID NO:76 |
| DRB1*0802 | Nonamer | 59 | IRPRSSQRV | 1.8 | SEQ ID NO:16 |
| DRB1*0802 | Nonamer | 123 | WLPKKCSLC | 2.3 | SEQ ID NO:78 |
| DRB1*0804 | Nonamer | 59 | IRPRSSQRV | 2.8 | SEQ ID NO:16 |
| DRB1*0806 | Nonamer | 59 | IRPRSSQRV | 3.1 | SEQ ID NO:16 |
| DRB1*1101 | Nonamer | 11 | YSVIWIMAI | 2.8 | SEQ ID NO:77 |
| DRB1*1101 | Nonamer | 152 | LVMDEHLVA | 2.2 | SEQ ID NO:75 |
| DRB1*1102 | Nonamer | 152 | LVMDEHLVA | 2.4 | SEQ ID NO:75 |
| DRB1*1104 | Nonamer | 25 | LGLVAGLGH | 2.8 | SEQ ID NO:79 |
| DRB1*1104 | Nonamer | 152 | LVMDEHLVA | 3.2 | SEQ ID NO:75 |
| DRB1*1106 | Nonamer | 25 | LGLVAGLGH | 2.8 | SEQ ID NO:79 |
| DRB1*1106 | Nonamer | 152 | LVMDEHLVA | 3.2 | SEQ ID NO:75 |
| DRB1*1107 | Nonamer | 46 | FRDDSIWPQ | 2.8 | SEQ ID NO:80 |
| DRB1*1107 | Nonamer | 152 | LVMDEHLVA | 5.9 | SEQ ID NO:75 |
| DRB1*1107 | Nonamer | 158 | LVASRTPEL | 3.3 | SEQ ID NO:76 |
| DRB1*1305 | Nonamer | 11 | YSVIWIMAI | 3.7 | SEQ ID NO:77 |
| DRB1*1307 | Nonamer | 11 | YSVIWIMAI | 1.2 | SEQ ID NO:77 |
| DRB1*1501 | Nonamer | 138 | LRCFPQAFL | 4.3 | SEQ ID NO:20 |
| DRB1*1501 | Nonamer | 152 | LVMDEHLVA | 4.5 | SEQ ID NO:75 |
| DRB1*1502 | Nonamer | 152 | LVMDEHLVA | 3.5 | SEQ ID NO:75 |
| DRB5*0101 | Nonamer | 13 | VIWIMAISK | 5.3 | SEQ ID NO:67 |

C-2 Cripto-1 Specific Class H Epitopes.

| HLA allele | Epitope size | Sequence position | Start | Score | SEQ ID NO: |
|---|---|---|---|---|---|
| DRB1*0101 | Nonamer | 15 | WIMAISKVF | 1.3 | SEQ ID NO:81 |
| DRB1*0102 | Nonamer | 176 | MLVGICLSI | 1.8 | SEQ ID NO:82 |
| DRB1*0102 | Nonamer | 178 | VGICLSIQS | 1.7 | SEQ ID NO:83 |
| DRB1*0301 | Nonamer | 17 | MAISKVFEL | 3.9 | SEQ ID NO:45 |
| DRB1*0401 | Nonamer | 178 | VGICLSIQS | 2.8 | SEQ ID NO:83 |
| DRB1*0402 | Nonamer | 178 | VGICLSIQS | 4.2 | SEQ ID NO:83 |
| DRB1*0404 | Nonamer | 14 | IWIMAISKV | 2.9 | SEQ ID NO:84 |
| DRB1*0404 | Nonamer | 177 | LVGICLSIQ | 3.3 | SEQ ID NO:85 |
| DRB1*0404 | Nonamer | 178 | VGICLSIQS | 3.8 | SEQ ID NO:83 |
| DRB1*0405 | Nonamer | 175 | FMLVGICLS | 3.2 | SEQ ID NO:86 |

-continued

| HLA allele | Epitope size | Sequence position | Start | Score | SEQ ID NO: |
|---|---|---|---|---|---|
| DRB1*0405 | Nonamer | 177 | LVGICLSIQ | 3.1 | SEQ ID NO:85 |
| DRB1*0405 | Nonamer | 178 | VGICLSIQS | 2.8 | SEQ ID NO:83 |
| DRB1*0703 | Nonamer | 15 | WIMAISKVF | 5.7 | SEQ ID NO:81 |
| DRB1*0703 | Nonamer | 17 | NAISKVFEL | 7.6 | SEQ ID NO:45 |
| DRB1*0703 | Nonamer | 176 | MLVGICLSI | 5 | SEQ ID NO:82 |
| DRB1*0801 | Nonamer | 175 | FMLVGICLS | 3.8 | SEQ ID NO:86 |
| DRB1*0802 | Nonamer | 175 | FMLVGICLS | 3.8 | SEQ ID NO:86 |
| DRB1*0804 | Nonamer | 175 | FMLVGICLS | 2.8 | SEQ ID NO:86 |
| DRB1*1101 | Nonamer | 175 | FMLVGICLS | 3.9 | SEQ ID NO:86 |
| DRB1*1101 | Nonamer | 178 | VGICLSIQS | 2.4 | SEQ ID NO:83 |
| DRB1*1104 | Nonamer | 175 | FMLVGICLS | 2.9 | SEQ ID NO:86 |
| DRB1*1104 | Nonamer | 177 | LVGICLSIQ | 2.6 | SEQ ID NO:85 |
| DRB1*1104 | Nonamer | 178 | VGICLSIQS | 3.4 | SEQ ID NO:83 |
| DRB1*1106 | Nonamer | 175 | FMLVGICLS | 2.9 | SEQ ID NO:86 |
| DRB1*1106 | Nonamer | 177 | LVGICLSIQ | 2.6 | SEQ ID NO:85 |
| DRB1*1106 | Nonamer | 178 | VGICLSIQS | 3.4 | SEQ ID NO:83 |
| DRB1*1107 | Nonamer | 17 | MAISKVFEL | 2.9 | SEQ ID NO:45 |
| DRB1*1107 | Nonamer | 177 | LVGICLSIQ | 3.6 | SEQ ID NO:85 |
| DRB1*1107 | Nonamer | 178 | VGICLSIQS | 3 | SEQ ID NO:83 |
| DRB1*1302 | Nonamer | 15 | WINAISKVF | 3.3 | SEQ ID NO:81 |
| DRB1*1302 | Nonamer | 175 | FMLVGICLS | 3 | SEQ ID NO:86 |
| DRB1*1305 | Nonamer | 15 | WIMAISKVF | 3.1 | SEQ ID NO:81 |
| DRB1*1305 | Nonamer | 175 | FMLVGICLS | 4.3 | SEQ ID NO:86 |
| DRB1*1307 | Nonamer | 175 | FMLVGICLS | 3.9 | SEQ ID NO:86 |
| DRB1*1307 | Nonamer | 177 | LVGICLSIQ | 1.6 | SEQ ID NO:85 |
| DRB1*1501 | Nonamer | 6 | MARFSYSVI | 4.5 | SEQ ID NO:43 |
| DRB1*1501 | Nonamer | 176 | MLVGICLSI | 4.1 | SEQ ID NO:82 |
| DRB1*1502 | Nonamer | 6 | MARFSYSVI | 3.5 | SEQ ID NO:43 |
| DRB5*0101 | Nonamer | 15 | WIMAISKVF | 4.1 | SEQ ID NO:81 |

C-2 Cripto-3 Specific Class II Epitopes.

| HLA allele | Epitope Start size | position | Sequence | SEQ ID Score | NO: |
|---|---|---|---|---|---|
| DRB1*0101 | Nonamer | 15 | WIMAISKAF | 1.3 | SEQ ID NO:87 |
| DRB1*0102 | Nonamer | 6 | MVRFSYSVI | 1.4 | SEQ ID NO:88 |
| DRB1*0102 | Nonamer | 17 | MAISKAFEL | 1:6 | SEQ ID NO:61 |
| DRB1*0401 | Nonamer | 7 | VRFSYSVIW | 2.9 | SEQ ID NO:51 |
| DRB1*0401 | Nonamer | 175 | FMLAGICLS | 2.7 | SEQ ID NO:89 |
| DRB1*0402 | Nonamer | 67 | VLPMGIQHS | 3.6 | SEQ ID NO:90 |
| DRB1*0404 | Nonamer | 6 | MVRFSYSVI | 2.5 | SEQ ID NO:88 |
| DRB1*0404 | Nonamer | 14 | IWIMAISKA | 3.6 | SEQ ID NO:91 |
| DRB1*0404 | Nonamer | 67 | VLPMGIQHS | 3.5 | SEQ ID NO:90 |
| DRB1*0405 | Nonamer | 175 | FMLAGICLS | 2.7 | SEQ ID NO:89 |
| DRB1*0703 | Nonamer | 7 | VRFSYSVIW | 6.5 | SEQ ID NO:51 |
| DRB1*0703 | Nonamer | 15 | WIMAISKAF | 5.7 | SEQ ID NO:87 |
| DRB1*0703 | Nonamer | 17 | MAISKAFEL | 7.5 | SEQ ID NO:61 |
| DRB1*0801 | Nonamer | 16 | IMAISKAFE | 3 | SEQ ID NO:92 |
| DRB1*0801 | Nonamer | 175 | FMLAGICLS | 3.5 | SEQ ID NO:89 |
| DRB1*0802 | Nonamer | 67 | VLPMGIQHS | 1.9 | SEQ ID NO:90 |
| DRB1*0802 | Nonamer | 175 | EMLAGICLS | 3.5 | SEQ ID NO:89 |
| DRB1*0804 | Nonamer | 67 | VLPMGIQHS | 2.9 | SEQ ID NO:90 |
| DRB1*0804 | Nonamer | 175 | FMLAGICLS | 2.5 | SEQ ID NO:89 |
| DRB1*0806 | Nonamer | 16 | IMAISKAFE | 4 | SEQ ID NO:92 |
| DRB1*1101 | Nonamer | 175 | FMLAGICLS | 3.5 | SEQ ID NO:89 |
| DRB1*1102 | Nonamer | 67 | VLPMGIQHS | 3.1 | SEQ ID NO:90 |
| DRB1*1102 | Nonamer | 175 | FMLAGICLS | 2.5 | SEQ ID NO:89 |
| DRB1*1107 | Nonamer | 7 | VRFSYSVIW | 2.8 | SEQ ID NO:51 |
| DRB1*1301 | Nonamer | 67 | VLPMGIQHS | 3.5 | SEQ ID NO:90 |
| DRB1*1302 | Nonamer | 15 | WIMAISKAF | 3.3 | SEQ ID NO:87 |
| DRB1*1302 | Nonamer | 175 | FMLAGICLS | 3.9 | SEQ ID NO:89 |
| DRB1*1305 | Nonamer | 15 | WIMAISKAF | 3.1 | SEQ ID NO:87 |
| DRB1*1305 | Nonamer | 175 | FMLAGICLS | 3.9 | SEQ ID NO:89 |
| DRB1*1307 | Nonamer | 67 | VLPMGIQRS | 1.5 | SEQ ID NO:90 |
| DRB1*1307 | Nonamer | 175 | FMLAGICLS | 3.5 | SEQ ID NO:89 |
| DRB1*1501 | Nonamer | 6 | MVRPSYSVI | 6.6 | SEQ ID NO:88 |
| DRB1*1502 | Nonamer | 6 | MVRFSYSVI | 5.6 | SEQ ID NO:88 |
| DRB5*0101 | Nonamer | 15 | WIMAISKAF | 4.1 | SEQ ID NO:87 |

EXAMPLE 5

Anti-Tumor Potential of the Humoral Response Induced by Cripto Vaccines

A series of experiments aimed at assessing the inhibitory effect of the Cripto-specific humoral response on the patho-physiological activities of Cripto in cancer could be carried out by using various standards in vitro assays. The in vitro assays could be, but not restricted to, growth inhibition assay, cell motility inhibition assay, chemotaxis inhibition assay, inhibition of the invasion through extracellular matrix protein (ECM), and growth signal transduction pathway inhibition. The effects of the sera of immunized animals with Cripto peptides or protein in adjuvant, or with a plasmid DNA or a viral delivery system, e.g. adenoviral vector, encoding the Cripto protein could be assessed in these in vitro assays that gauge Cripto-mediated biological effects on Cripto-expressing cell lines. In parallel, the effect of the pre-immune sera from the same animals will be tested as negative control. The cell lines used in these assays could be, but not limited to, human tumor cells expressing Cripto such as GEO cells, NTERA2 cells, the CRL-5815 cell line, or murine tumor cell lines that naturally over-express Cripto. As example, the inhibition of the in vitro growth of both GEO and NTERA2 cells has previously been demonstrated by treatment with antisense oligonucleotides designed to prevent the translation of Cripto mRNA [Baldassarre et al., 1996; Ciardiello et al., 1994; Alper et al., 2000].

5.1: Immunization Protocol:

Mice or rabbits would be immunized on day 0, 14, and 21 by intra-footpad injections of either peptides or protein in adjuvant, intra-dermal injections of a plasmid DNA encoding Cripto using gene-gun devices, or intra-dermal injections of a viral vector delivery system, e.g. adenoviral vector, encoding Cripto.

5.2: Cell Proliferation Inhibition Assay:

The sera from immunized animals will be collected and added at different dilutions to the culture medium of cells platted in 96-well plates. Similarly, pre-immune sera of these animals will also be added to cells as negative control. The cells will be treated for 3 to 7 days. The cell growth will be measured by standard methods such as $^3$H-thymidine incorporation assay, MTT assay, crystal violet staining, or colony counting for proliferation in soft agar-medium.

5.3: Cell Invasion, Motility, and Chemotaxis Inhibition Assays:

The sera from immunized animals will be collected pre- and post-immunization and added at different dilutions to cell suspensions used for invasion, motility, and chemotaxis standards assays. The inhibition of Cripto-mediated invasion, motility, and chemotaxis could be assessed with the use of, for instance, but limited to, commercially available Falcon chambers with matrigel inserts (Collaborative Research), agarose droplet motility assay [Yamamoto et al., 1990], and commercially available Boyden apparatus (Neuro Probe), respectively.

5.4: Signal Transduction Inhibition Assays:

The sera from immunized animals will be collected pre- and post-immunization and added at different dilutions to Cripto-expressing tumor cells in culture. Then, exogenous Cripto protein or human sera or milk containing the highest concentration of Cripto detected by ELISA [Bianco et al., 2001] will be added to the culture medium of the cells. After various incubation times, the cells will be harvested and processed by standard methods in order to perform immunoblot analysis. The phosphorylation status of various key signal transduction pathways involved in cell proliferation will be assessed in these Cripto-simulated cells in the presence of pre- or post-immune sera. For instance, the tyrosine phosphorlation status of erb B-4 and mitogen-activated protein (MAP) kinase family such as ERK1, ERK-2, and P38 will be assessed by immunoblotting with antibodies that recognize the phosphorylated, active form of these enzymes as previous described [Bianco et al., 1999;Paine et al., 2000].

EXAMPLE 6

In Vivo Anti-Tumor Effect of the Immune Response Induced by Cripto Vaccines in Animal Models The prophylactic or therapeutic potential of vaccines containing the human Cripto protein, Cripto peptides, or Cripto gene can be evaluated in mice challenged with syngeneic murine tumor cell line that express Cripto. The tumor cell lines could be a murine tumor cell line transfected with the human Cripto gene. For instance the transfected cell lines could be the TC1 cell line transfected with human Cripto gene. On the other hand, the high level of homology between human Cripto and its murine homologue suggests that cross-reactive immune responses induced by the human vaccine can protect against mouse Cripto-expressing tumors. Indeed, Cripto gene (TDGF-1) encodes a 171-amino acid protein which has 93% identity with its human counterpart [Liguori et al., 1996]. Therefore mice could be protected by immunization with a human Critpo vaccine from murine tumor challenge or spontaneously arising tumor known to endogenously over-express the Cripto protein. With this respect, spontaneous tumors in transgenic mice designed to over-express several different oncogenes such as MMTV-Polyoma virus middle T antigen, MMTV-c-ErbB2, and MT-hTGF alpha, have been shown also to over-express Cripto [Kenney et al., 1996;Niemeyer et al., 1999].

Alternatively, in order to vaccinate with the syngeneic gene, the tumor-bearing mice could be vaccinated with a plasmid DNA or a viral delivery system, e.g. adenoviral vector, encoding the murine Cripto protein to protect from murine tumor growth.

6.1: Prophylactic Experimental Design:

Mice would be vaccinated on day 0 and 14, prior tumor challenge, by either intra-footpad injections of 5 μg of Cripto protein in adjuvant, intra-dermal injections of DNA plasmid encoding Cripto using gene-gun technology, or intra-dermal injections of a viral vector, e.g. adenoviral vector, encoding Cripto. Then, $10^6$ TC1-CR-1 cells, human Cripto-expressing tumor cells, could be injected subcutaneously in the flank of C57BL/6 immunocompetent mice 1 or 2 weeks post vaccination. The tumor growth should be monitored in vivo by measuring individual tumors twice a week for several weeks post-tumor challenge.

On the other hand, the efficacy of prophylactic vaccination could be assessed by inhibiting the development of spontaneous Cripto-expressing tumors in transgenic mice [Niemeyer et al., 1999] immunized multiple times before onset of the palpable tumor with either form of Cripto vaccines.

6.2: Therapeutic Experimental Design:

$10^6$ TC1-CR-1 cells, human-Critpo expressing tumor cells, would be injected subcutaneously in the flank of C57BL/6 immunocompetent mice. Mice could be vaccinated on days 7 and 14, post-tumor challenge, by either intra-footpad injections of 5 μg Cripto protein in adjuvant, intra-dermal injections of DNA plasmid encoding Cripto using gene-gun technology, or intra-dermal injections of a viral vector, e.g. adenoviral vector, encoding Cripto. The tumor growth should be monitored in vivo by measuring individual tumors twice a week. One to 4 weeks after the second immunization, several mice per group will be sacrificed to harvest spleen cells, draining lymph nodes, and sera for analysis of the immune responses to establish a correlation between the induction of a Cripto-specific immune response and the anti-tumor effect. The analysis of the Cripto-specific immune response induced by immunization could be assessed by measuring the antibody titers, antibody isotypic profile, the $CD4^+$ T-cell proliferation response, and CTL $CD8^+$ T-cell responses including cytokines production and lysis activity against Cripto-expressing target cells. All assays would be performed according to standards protocols.

A similar kind of experiment could be carried out by challenging parental mice with transplantable murine mammary tumor lines over-expressing Cripto. These cells would be established from spontaneous tumor arising in various oncogene transgenic mouse strains such as MMTV-Polyoma virus middle T antigen, MMTV-c-ErbB2, and MT-hTGF alpha transgenic mice [Niemeyer et al., 1999].

REFERENCES

Alper O, De Santis M L, Stromberg K, Hacker N F, Cho-Chung Y S, Salomon D S (2000) Anti-sense suppression of epidermal growth factor receptor expression alters cellular proliferation, cell-adhesion and tumorigenicity in ovarian cancer cells. *Int J Cancer* 88: 566-574

Baldassarre G, Bianco C, Tortora G, Ruggiero A, Moasser M, Dmitrovsky E, Bianco A R, Ciardiello F (1996) Transfection with a CRIPTO anti-sense plasmid suppresses endogenous CRIPTO expression and inhibits transformation in a human embryonal carcinoma cell line. *Int J Cancer* 66: 538-543

Bianco C, Kannan S, De Santis M, Seno M, Tang C K, Martinez-Lacaci I, Kim N, Wallace-Jones B, Lippman M E, Ebert A D, Wechselberger C, Salomon D S (1999) Cripto-1 indirectly stimulates the tyrosine phosphorylation of erb B-4 through a novel receptor. *J Biol Chem* 274: 8624-8629

Bianco C, Wechselberger C, Ebert A, Khan N I, Sun Y, Salomon D S (2001) Identification of Cripto-1 in human milk. *Breast Cancer Res Treat* 66: 1-7

Butterfield L H, Jilani S M, Chakraborty N G, Bui L A, Ribas A, Dissette V B, Lau R, Gamradt S C, Glaspy J A, McBride W H, Mukherji B, Economou J S. (1998) Generation of melanoma-specific cytotoxic T lymphocytes by dendritic cells transduced with a MART-1 adenovirus. *J Immunol.* 161: 5607-13.

Ciardiello F, Tortora G, Bianco C, Selvam M P, Basolo F, Pontanini G, Pacifico F, Normamo N, Brandt R, Persico M G (1994) Inhibition of CRIPTO expression and tumorigenicity in human colon cancer cells by antisense RNA and oligodeoxynucleotides. *Oncogene* 9: 291-298

Kenney N J, Smith G H, Maroulakou I G, Green J H, Muller W J, Callahan R, Salomon D S, Dickson R B (1996) Detection of amphiregulin and Cripto-1 in mammary tumors from transgenic mice. *Mol Carcinog* 15: 44-56

Kim C J, Prevette T, Cormier J, Overwijk W, Roden M, Restifo N P, Rosenberg S A, Marincola F M. (1997) Dendritic cells infected with poxviruses encoding MART-1/Melan A sensitize T lymphocytes in vitro. *J Iminunother.*20:276-286.

Liguori G, Tucci M, Montuori N, Dono R, Lago C T, Pacifico F, Armenante F, Persico M G (1996) Characterization of the mouse Tdgf1 gene and Tdgf pseudogenes. *Mamm Genome* 7: 344-348

Niemeyer CC, Spencer-Dene B, Wu J X, Adamson E D (1999) Preneoplastic mammary tumor markers: Cripto and Amphiregulin are overexpressed in hyperplastic stages of tumor progression in transgenic mice. *Int J Cancer* 81: 588-591

Paine E, Palmantier R, Akiyama S K, Olden K, Roberts J D (2000) Arachidonic acid activates mitogen-activated protein (MAP) kinase-activated protein kinase 2 and mediates adhesion of a human breast carcinoma cell line to collagen type IV through a p38 MAP kinase-dependent pathway. *J Biol Chem* 275: 11284-11290

Parker K, Bednarek M, Coligan J (1994). Scheme for ranking potential HLA-A2 binding peptides based on independent binding of individual peptide side-chains. *J. Immunol.* 152: 163.

Rammensee, Bachmann, Stevanovic (1997). MHC ligands and peptide motifs. *Landes Bioscience.*

Rammensee, Friede, Stevanovic (1995). MHC ligands and peptide motifs: 1st listing, *Immunogenetics* 41, 178-228.

Romani N, Gruner S, Brang D, Kampgen E, Lenz A, Trockenbacher B, Konwalinka G, Fritsch P O, Steinman R M, Schuler G. (1994) Proliferating dendritic cell progenitors in human blood. *J Exp Med.* 180:83-93.

Sturniolo T, Bono E, Ding J, Raddrizzani L, Tuereci O, Sahin U, Braxenthaler M, Gallazzi F, Protti M P, Sinigaglia F, Hammer J. (1999) Generation of tissue-specific and promiscuous HLA ligand databases using DNA microarrays and virtual HLA class II matrices. *Nat Biotechnol.* 17: 555-61.

Yamamoto T, Varani J, Soong H K, Lichter P R (1990) Effects of 5-fluorouracil and mitomycin C on cultured rabbit subconjunctival fibroblasts. *Ophthalmology* 97: 1204-1210

The invention claimed is:

1. An immunogenic composition comprising:

(a) a component selected from the group consisting of: physiologically acceptable carriers, immunostimulants, and adjuvants; and (b) a polypeptide selected from the group consisting of:

(i) a polypeptide consisting of the amino acid sequence of SEQ ID NO:11; and (ii) a polypeptide consisting of the amino acid sequence of SEQ ID NO:12.

2. The immunogenic composition according to claim 1 comprising a TH-1 inducing adjuvant.

3. The immunogenic composition according to claim 2 wherein the TH-1 inducing adjuvant is selected from 3D-MPL, QS21, a mixture of QS21 and cholesterol, a CpG oligonucleotide, and a mixture of two or more of said adjuvants.

* * * * *

SEQUENCE LISTING

```
<160> NUMBER OF SEQ ID NOS: 96

<210> SEQ ID NO 1
<211> LENGTH: 2033
<212> TYPE: DNA
<213> ORGANISM: human

<400> SEQUENCE: 1

ggagaatccc cggaaaggct gagtctccag ctcaaggtca aaacgtccaa ggccgaaagc      60

cctccagttt cccctggacg ccttgctcct gcttctgcta cgaccttctg gggaaaacga     120

atttctcatt ttcttcttaa attgccattt tcgctttagg agatgaatgt tttcctttgg     180

ctgttttggc aatgactctg aattaaagcg atgctaacgc ctcttttccc cctaattgtt     240
```

-continued

```
aaaagctatg gactgcagga agatggcccg cttctcttac agtgtgattt ggatcatggc    300

catttctaaa gtctttgaac tgggattagt tgccgggctg ggccatcagg aatttgctcg    360

tccatctcgg ggatacctgg ccttcagaga tgacagcatt tggccccagg aggagcctgc    420

aattcggcct cggtcttccc agcgtgtgcc gcccatgggg atacagcaca gtaaggagct    480

aaacagaacc tgctgcctga atgggggaac ctgcatgctg gggtcctttt gtgcctgccc    540

tccctccttc tacggacgga actgtgagca cgatgtgcgc aaagagaact gtgggtctgt    600

gccccatgac acctggctgc ccaagaagtg ttccctgtgt aaatgctggc acggtcagct    660

ccgctgcttt cctcaggcat ttctacccgg ctgtgatggc cttgtgatgg atgagcacct    720

cgtggcttcc aggactccag aactaccacc gtctgcacgt actaccactt ttatgctagt    780

tggcatctgc ctttctatac aaagctacta ttaatcgaca ttgacctatt tccagaaata    840

caattttaga tatcatgcaa atttcatgac cagtaaaggc tgctgctaca atgtcctaac    900

tgaaagatga tcatttgtag ttgccttaaa ataatgaata caatttccaa aatggtctct    960

aacatttcct tacagaacta cttcttactt ctttgccctg ccctctccca aaaaactact   1020

tctttttttca aaagaaagtc agccatatct ccattgtgcc taagtccagt gtttcttttt   1080

ttttttttt ttgagacgga gtctcactct gtcacccagg ctggactgca atgacgcgat   1140

cttggttcac tgcaacctcc gcatccgggg ttcaagccat tctcctgcct aagcctccca   1200

agtaactggg attacaggca tgtgtcacca tgcccagcta attttttttgt attttagtag   1260

agatgggggt ttcaccatat tggccagtct ggtctcgaac tctgaccttg tgatccatcg   1320

atcagcctct cgagtgctga gattacacac gtgagcaact gtgcaaggcc tggtgtttct   1380

tgatacatgt aattctacca aggtcttctt aatatgttct tttaaatgat tgaattatat   1440

gttcagatta ttggagacta attctaatgt ggaccttaga atacagtttt gagtagagtt   1500

gatcaaaatc aattaaaata gtctctttaa aaggaaagaa aacatcttta aggggaggaa   1560

ccagagtgct gaaggaatgg aagtccatct gcgtgtgtgc agggagactg ggtaggaaag   1620

aggaagcaaa tagaagagag aggttgaaaa acaaaatggg ttacttgatt ggtgattagg   1680

tggtggtaga gaagcaagta aaaaggctaa atggaagggc aagtttccat catctataga   1740

aagctatata agacaagaac tccccttttt ttcccaaagg cattataaaa agaatgaagc   1800

ctccttagaa aaaaaattat acctcaatgt ccccaacaag attgcttaat aaattgtgtt   1860

tcctccaagc tattcaattc ttttaactgt tgtagaagac aaaatgttca caatatattt   1920

agttgtaaac caagtgatca aactacatat tgtaaagccc atttttaaaa tacattgtat   1980

atatgtgtat gcacagtaaa aatggaaact atattgacct aaaaaaaaaa aaa          2033
```

<210> SEQ ID NO 2
<211> LENGTH: 2688
<212> TYPE: DNA
<213> ORGANISM: human
<220> FEATURE:
<222> LOCATION: 2675, 2676
<223> OTHER INFORMATION: n can be any of a, t, g and c nucleotide base.

<400> SEQUENCE: 2

```
aagcttgcgc gccatgtaag gtaaagtgac tgattctata gcaatccaat tgttcctttg     60

tctgcccgtt tacatataac aatgttgtca atgtttgatt gaaaatacct agcaggcgac    120

acacacacac ctagctcctc aggcggagag cacccctttc ttggccaccc gggtatcccc    180

cagggagtac ggggctcaaa acacccctttt ggagaacaag gtggaagcaa atttcaggaa    240
```

-continued

```
gtaaaacttc ctgaaataaa ataaaatatc gaatgccttg agacccatac attttcaggt    300
tttcctaatt aaagcaatta ctttccacca cccctccaac ctggaatcac caacttggtt    360
agagaaactg atttttcttt tttcttttt tttcccaaaa gagtacatct gatcatttta    420
gcctgcaact aatgatagag atattagggc tagttaacca cagttttaca agactcctct    480
cccgcgtgtg ggccattgtc atgctgtcgg tcccgcccac ctgaaaggtc tccccgcccc    540
gactggggtt tgttgttgaa gaaggagaat ccccggaaag gctgagtctc cagctcaagg    600
tcaaaacgtc caaggccgaa agccctccag tttcccctgg acaccttgct cctgcttctg    660
ctacgacctt ctgggaacgc gaatttctca ttttcttctt aaattgccat tttcgcttta    720
ggagatgaat gttttccttt ggctgttttg gcaatgactc tgaattaaag cgatgctaac    780
gcctcttttc cccctaattg ttaaaagcta tggactgcag gaagatggtc cgcttctctt    840
acagtgtgat ttggatcatg gccatttcta aagcctttga actgggatta gttgccgggc    900
tgggccatca ggaatttgct cgtccatctc ggggagacct ggccttcaga gatgacagca    960
tttggcccca ggaggagcct gcaattcggc ctcggtcttc ccagcgtgtg ctgcccatgg   1020
gaatacagca cagtaaggag ctaaacagaa cctgctgcct gaatgggga acctgcatgc   1080
tggagtcctt ttgtgcctgc cctccctcct tctacggacg gaactgtgag cacgatgtgc   1140
gcaaagagaa ctgtgggtct gtgccccatg acacctggct gcccaagaag tgttccctgt   1200
gtaaatgctg gcacggtcag ctccgctgct ttcctcaggc atttctaccc ggctgtgatg   1260
gccttgtgat ggatgagcac ctcgtggctt ccaggactcc agaactacca ccgtctgcac   1320
gtactaccac ttttatgcta gctggcatct gcctttctat acaaagctac tattaatcga   1380
cattgaccta tttccagaaa tacaatttta gatattatgc aaatttcatg acccgtaaag   1440
gctgctgcta caatgtccta actgaaagat gatcatttgt agttgcctta aaataatgaa   1500
tacaatttcc aaaacggtct ctaacatttc cttacagaac taactacttc ttacctcttt   1560
gccctgccct ctcccaaaaa actacttctt ttttcaaaag aaagtcagcc atatctccat   1620
tgtgcccaag tccagtgttt cttttttttt tttgagacgg agtctcactc tgtcacccag   1680
gctggactgc aatgacgcga tctcggttca ctgcaacctc cgcatccggg gttcaagcca   1740
ttctcctgcc tcagcctccc aagtagctgg gattacaggc atgtgtcacc atgccggcta   1800
atttttttgt attttagtag agacgggggt ttcaccatat tggccagctg gtctcgaact   1860
ctgaccttgt gatccatcgc tcgcctctcg agtgctgaga ttacacacgt gagcaactgt   1920
gcaaggcctg gtgtttcttg atacatgtaa ttctaccaag gtcttcttaa tatgttcttt   1980
taaatgattg aattatacac tcagattatt ggagactaag tctaatgtgg accttagaat   2040
acagttttga gtagagttga tcaaaatcaa ttaaaatagt ctctttaaaa ggaaagaaaa   2100
catctttaag gggaggaacc agagtgctga aggaatggaa gtccatctgc gtgtgtgcag   2160
ggagactggg taggaaagag gaagcaaata gaagagagag gttgaaaaac aaaatgggtt   2220
acttgattgg tgattaggtg gtggtagaga agcaagtaaa aaggctaaat ggaagggcaa   2280
gtttccatca tctatagaaa gctatgtaag acaaggactc cccttttttt cccaaaggca   2340
ttgtaaaaag aatgaagtct ccttagaaaa aaaattatac ctcaatgtcc ccaacaagat   2400
tgcttaataa attgtgtttc ctccaagcta ttcaattctt ttaactgttg tagaagagaa   2460
aatgttcaca atatatttag ttgtaaacca agtgatcaaa ctacatattg taaagcccat   2520
ttttaaaata cattgtatat atgtgtatgc acagtaaaaa tggaaactat attgacctaa   2580
```

-continued

```
aaaaaaaaaa aggaaaccac ccttaggcag gcaggacatg ctcttcagaa ctctgctctt   2640

cagagttcca aagaagggat aaaacatctt ttatnnccat caaatagc                2688


<210> SEQ ID NO 3
<211> LENGTH: 188
<212> TYPE: PRT
<213> ORGANISM: Human

<400> SEQUENCE: 3

Met Asp Cys Arg Lys Met Ala Arg Phe Ser Tyr Ser Val Ile Trp Ile
 1               5                  10                  15

Met Ala Ile Ser Lys Val Phe Glu Leu Gly Leu Val Ala Gly Leu Gly
            20                  25                  30

His Gln Glu Phe Ala Arg Pro Ser Arg Gly Tyr Leu Ala Phe Arg Asp
        35                  40                  45

Asp Ser Ile Trp Pro Gln Glu Glu Pro Ala Ile Arg Pro Arg Ser Ser
    50                  55                  60

Gln Arg Val Pro Pro Met Gly Ile Gln His Ser Lys Glu Leu Asn Arg
65                  70                  75                  80

Thr Cys Cys Leu Asn Gly Gly Thr Cys Met Leu Gly Ser Phe Cys Ala
                85                  90                  95

Cys Pro Pro Ser Phe Tyr Gly Arg Asn Cys Glu His Asp Val Arg Lys
            100                 105                 110

Glu Asn Cys Gly Ser Val Pro His Asp Thr Trp Leu Pro Lys Lys Cys
        115                 120                 125

Ser Leu Cys Lys Cys Trp His Gly Gln Leu Arg Cys Phe Pro Gln Ala
    130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Thr Phe Met
                165                 170                 175

Leu Val Gly Ile Cys Leu Ser Ile Gln Ser Tyr Tyr
            180                 185


<210> SEQ ID NO 4
<211> LENGTH: 188
<212> TYPE: PRT
<213> ORGANISM: human

<400> SEQUENCE: 4

Met Asp Cys Arg Lys Met Val Arg Phe Ser Tyr Ser Val Ile Trp Ile
 1               5                  10                  15

Met Ala Ile Ser Lys Ala Phe Glu Leu Gly Leu Val Ala Gly Leu Gly
            20                  25                  30

His Gln Glu Phe Ala Arg Pro Ser Arg Gly Asp Leu Ala Phe Arg Asp
        35                  40                  45

Asp Ser Ile Trp Pro Gln Glu Glu Pro Ala Ile Arg Pro Arg Ser Ser
    50                  55                  60

Gln Arg Val Leu Pro Met Gly Ile Gln His Ser Lys Glu Leu Asn Arg
65                  70                  75                  80

Thr Cys Cys Leu Asn Gly Gly Thr Cys Met Leu Glu Ser Phe Cys Ala
                85                  90                  95

Cys Pro Pro Ser Phe Tyr Gly Arg Asn Cys Glu His Asp Val Arg Lys
            100                 105                 110

Glu Asn Cys Gly Ser Val Pro His Asp Thr Trp Leu Pro Lys Lys Cys
        115                 120                 125
```

-continued

```
Ser Leu Cys Lys Cys Trp His Gly Gln Leu Arg Cys Phe Pro Gln Ala
    130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Thr Phe Met
                165                 170                 175

Leu Ala Gly Ile Cys Leu Ser Ile Gln Ser Tyr Tyr
            180                 185


<210> SEQ ID NO 5
<211> LENGTH: 2033
<212> TYPE: DNA
<213> ORGANISM: human

<400> SEQUENCE: 5

ggagaatccc cggaaaggct gagtctccag ctcaaggtca aaacgtccaa ggccgaaagc     60

cctccagttt cccctggacg ccttgctcct gcttctgcta cgaccttctg ggaaaaacga    120

atttctcatt ttcttcttaa attgccattt tcgctttagg agatgaatgt tttcctttgg    180

ctgttttggc aatgactctg aattaaagcg atgctaacgc ctcttttccc cctaattgtt    240

aaaagctatg gactgcagga agatggcccg cttctcttac agtgtgattt ggatcatggc    300

catttctaaa gtctttgaac tgggattagt tgccgggctg ggccatcagg aatttgctcg    360

tccatctcgg ggatacctgg ccttcagaga tgacagcatt tggccccagg aggagcctgc    420

aattcggcct cggtcttccc agcgtgtgcc gcccatgggg atacagcaca gtaaggagct    480

aaacagaacc tgctgcctga atgggggaac ctgcatgctg gggtcctttt gtgcctgccc    540

tccctccttc tacggacgga actgtgagca cgatgtgcgc aaagagaact gtgggtctgt    600

gccccatgac acctggctgc ccaagaagtg ttccctgtgt aaatgctggc acggtcagct    660

ccgctgcttt cctcaggcat ttctacccgg ctgtgatggc cttgtgatgg atgagcacct    720

cgtggcttcc aggactccag aactaccacc gtctgcacgt actaccactt ttatgctagt    780

tggcatctgc ctttctatac aaagctacta ttaatcgaca ttgacctatt tccagaaata    840

caattttaga tatcatgcaa atttcatgac cagtaaaggc tgctgctaca atgtcctaac    900

tgaaagatga tcatttgtag ttgccttaaa ataatgaata caatttccaa aatggtctct    960

aacatttcct tacagaacta cttcttactt ctttgccctg ccctctccca aaaaactact   1020

tctttttca aaagaaagtc agccatatct ccattgtgcc taagtccagt gtttcttttt    1080

ttttttttt ttgagacgga gtctcactct gtcacccagg ctggactgca atgacgcgat    1140

cttggttcac tgcaacctcc gcatccgggg ttcaagccat tctcctgcct aagcctccca   1200

agtaactggg attacaggca tgtgtcacca tgcccagcta atttttttgt attttagtag   1260

agatgggggt ttcaccatat tggccagtct ggtctcgaac tctgaccttg tgatccatcg   1320

atcagcctct cgagtgctga gattacacac gtgagcaact gtgcaaggcc tggtgtttct   1380

tgatacatgt aattctacca aggtcttctt aatatgttct tttaaatgat tgaattatat   1440

gttcagatta ttggagacta attctaatgt ggaccttaga atacagtttt gagtagagtt   1500

gatcaaaatc aattaaaata gtctctttaa aaggaaagaa aacatcttta aggggaggaa   1560

ccagagtgct gaaggaatgg aagtccatct gcgtgtgtgc agggagactg ggtaggaaag   1620

aggaagcaaa tagaagagag aggttgaaaa acaaaatggg ttacttgatt ggtgattagg   1680

tggtggtaga gaagcaagta aaaaggctaa atggaagggc aagtttccat catctataga   1740
```

-continued

```
aagctatata agacaagaac tccccttttt ttcccaaagg cattataaaa agaatgaagc   1800

ctccttagaa aaaaaattat acctcaatgt ccccaacaag attgcttaat aaattgtgtt   1860

tcctccaagc tattcaattc ttttaactgt tgtagaagac aaaatgttca caatatattt   1920

agttgtaaac caagtgatca aactacatat tgtaaagccc atttttaaaa tacattgtat   1980

atatgtgtat gcacagtaaa aatggaaact atattgacct aaaaaaaaaa aaa          2033
```

<210> SEQ ID NO 6
<211> LENGTH: 188
<212> TYPE: PRT
<213> ORGANISM: human

<400> SEQUENCE: 6

```
Met Asp Cys Arg Lys Met Ala Arg Phe Ser Tyr Ser Val Ile Trp Ile
 1               5                  10                  15

Met Ala Ile Ser Lys Val Phe Glu Leu Gly Leu Val Ala Gly Leu Gly
            20                  25                  30

His Gln Glu Phe Ala Arg Pro Ser Arg Gly Tyr Leu Ala Phe Arg Asp
        35                  40                  45

Asp Ser Ile Trp Pro Gln Glu Glu Pro Ala Ile Arg Pro Arg Ser Ser
    50                  55                  60

Gln Arg Val Pro Pro Met Gly Ile Gln His Ser Lys Glu Leu Asn Arg
65                  70                  75                  80

Thr Cys Cys Leu Asn Gly Gly Thr Cys Met Leu Gly Ser Phe Cys Ala
                85                  90                  95

Cys Pro Pro Ser Phe Tyr Gly Arg Asn Cys Glu His Asp Val Arg Lys
            100                 105                 110

Glu Asn Cys Gly Ser Val Pro His Asp Thr Trp Leu Pro Lys Lys Cys
        115                 120                 125

Ser Leu Cys Lys Cys Trp His Gly Gln Leu Arg Cys Phe Pro Gln Ala
    130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Thr Phe Met
                165                 170                 175

Leu Val Gly Ile Cys Leu Ser Ile Gln Ser Tyr Tyr
            180                 185
```

<210> SEQ ID NO 7
<211> LENGTH: 23
<212> TYPE: DNA
<213> ORGANISM: human

<400> SEQUENCE: 7

```
tgggtaggaa agaggaagca aat                                              23
```

<210> SEQ ID NO 8
<211> LENGTH: 24
<212> TYPE: DNA
<213> ORGANISM: human

<400> SEQUENCE: 8

```
tgcttctcta ccaccaccta atca                                             24
```

<210> SEQ ID NO 9
<211> LENGTH: 26
<212> TYPE: DNA
<213> ORGANISM: human

-continued

<400> SEQUENCE: 9
cgtccaaggc cgaaagccct ccagtt 26

<210> SEQ ID NO 10
<211> LENGTH: 30
<212> TYPE: DNA
<213> ORGANISM: human

<400> SEQUENCE: 10
ttgggagagg gcagggcaaa gaagtaagaa 30

<210> SEQ ID NO 11
<211> LENGTH: 13
<212> TYPE: PRT
<213> ORGANISM: human

<400> SEQUENCE: 11

Gly His Gln Glu Phe Ala Arg Pro Ser Arg Gly Tyr Leu
1 5 10

<210> SEQ ID NO 12
<211> LENGTH: 18
<212> TYPE: PRT
<213> ORGANISM: human

<400> SEQUENCE: 12

Gln Glu Glu Pro Ala Ile Arg Pro Arg Ser Ser Gln Arg Val Pro Pro
1 5 10 15

Met Gly

<210> SEQ ID NO 13
<211> LENGTH: 10
<212> TYPE: PRT
<213> ORGANISM: human

<400> SEQUENCE: 13

Ser Val Ile Trp Ile Met Ala Ile Ser Lys
1 5 10

<210> SEQ ID NO 14
<211> LENGTH: 10
<212> TYPE: PRT
<213> ORGANISM: human

<400> SEQUENCE: 14

Ser Val Pro His Asp Thr Trp Leu Pro Lys
1 5 10

<210> SEQ ID NO 15
<211> LENGTH: 9
<212> TYPE: PRT
<213> ORGANISM: human

<400> SEQUENCE: 15

His Gln Glu Phe Ala Arg Pro Ser Arg
1 5

<210> SEQ ID NO 16
<211> LENGTH: 9
<212> TYPE: PRT
<213> ORGANISM: human

<400> SEQUENCE: 16

-continued

```
Ile Arg Pro Arg Ser Ser Gln Arg Val
 1               5


<210> SEQ ID NO 17
<211> LENGTH: 9
<212> TYPE: PRT
<213> ORGANISM: human

<400> SEQUENCE: 17

Ile Gln His Ser Lys Glu Leu Asn Arg
 1               5


<210> SEQ ID NO 18
<211> LENGTH: 9
<212> TYPE: PRT
<213> ORGANISM: human

<400> SEQUENCE: 18

Gly Arg Asn Cys Glu His Asp Val Arg
 1               5


<210> SEQ ID NO 19
<211> LENGTH: 9
<212> TYPE: PRT
<213> ORGANISM: human

<400> SEQUENCE: 19

Val Arg Lys Glu Asn Cys Gly Ser Val
 1               5


<210> SEQ ID NO 20
<211> LENGTH: 9
<212> TYPE: PRT
<213> ORGANISM: human

<400> SEQUENCE: 20

Leu Arg Cys Phe Pro Gln Ala Phe Leu
 1               5


<210> SEQ ID NO 21
<211> LENGTH: 9
<212> TYPE: PRT
<213> ORGANISM: human

<400> SEQUENCE: 21

Ser Arg Thr Pro Glu Leu Pro Pro Ser
 1               5


<210> SEQ ID NO 22
<211> LENGTH: 10
<212> TYPE: PRT
<213> ORGANISM: human

<400> SEQUENCE: 22

Gln Arg Val Pro Pro Met Gly Ile Gln His
 1               5                  10


<210> SEQ ID NO 23
<211> LENGTH: 10
<212> TYPE: PRT
<213> ORGANISM: human

<400> SEQUENCE: 23

Asn Arg Thr Cys Cys Leu Asn Gly Gly Thr
```

-continued 1 5 10

<210> SEQ ID NO 24
<211> LENGTH: 10
<212> TYPE: PRT
<213> ORGANISM: human

<400> SEQUENCE: 24

Gly Gln Leu Arg Cys Phe Pro Gln Ala Phe
1 5 10

<210> SEQ ID NO 25
<211> LENGTH: 10
<212> TYPE: PRT
<213> ORGANISM: human

<400> SEQUENCE: 25

Gln Ala Phe Leu Pro Gly Cys Asp Gly Leu
1 5 10

<210> SEQ ID NO 26
<211> LENGTH: 10
<212> TYPE: PRT
<213> ORGANISM: human

<400> SEQUENCE: 26

Asp Gly Leu Val Met Asp Glu His Leu Val
1 5 10

<210> SEQ ID NO 27
<211> LENGTH: 9
<212> TYPE: PRT
<213> ORGANISM: human

<400> SEQUENCE: 27

Phe Glu Leu Gly Leu Val Ala Gly Leu
1 5

<210> SEQ ID NO 28
<211> LENGTH: 9
<212> TYPE: PRT
<213> ORGANISM: human

<400> SEQUENCE: 28

Lys Glu Leu Asn Arg Thr Cys Cys Leu
1 5

<210> SEQ ID NO 29
<211> LENGTH: 9
<212> TYPE: PRT
<213> ORGANISM: human

<400> SEQUENCE: 29

Gln Leu Arg Cys Phe Pro Gln Ala Phe
1 5

<210> SEQ ID NO 30
<211> LENGTH: 9
<212> TYPE: PRT
<213> ORGANISM: human

<400> SEQUENCE: 30

Ser Ala Arg Thr Thr Thr Phe Met Leu
1 5

-continued

<210> SEQ ID NO 31
<211> LENGTH: 9
<212> TYPE: PRT
<213> ORGANISM: human

<400> SEQUENCE: 31

Lys Met Ala Arg Phe Ser Tyr Ser Val
1 5

<210> SEQ ID NO 32
<211> LENGTH: 10
<212> TYPE: PRT
<213> ORGANISM: human

<400> SEQUENCE: 32

Ile Met Ala Ile Ser Lys Val Phe Glu Leu
1 5 10

<210> SEQ ID NO 33
<211> LENGTH: 10
<212> TYPE: PRT
<213> ORGANISM: human

<400> SEQUENCE: 33

Val Ile Trp Ile Met Ala Ile Ser Lys Val
1 5 10

<210> SEQ ID NO 34
<211> LENGTH: 10
<212> TYPE: PRT
<213> ORGANISM: human

<400> SEQUENCE: 34

Phe Met Leu Val Gly Ile Cys Leu Ser Ile
1 5 10

<210> SEQ ID NO 35
<211> LENGTH: 9
<212> TYPE: PRT
<213> ORGANISM: human

<400> SEQUENCE: 35

Ala Arg Phe Ser Tyr Ser Val Ile Trp
1 5

<210> SEQ ID NO 36
<211> LENGTH: 9
<212> TYPE: PRT
<213> ORGANISM: human

<400> SEQUENCE: 36

Cys Arg Lys Met Ala Arg Phe Ser Tyr
1 5

<210> SEQ ID NO 37
<211> LENGTH: 10
<212> TYPE: PRT
<213> ORGANISM: human

<400> SEQUENCE: 37

Ala Arg Phe Ser Tyr Ser Val Ile Trp Ile
1 5 10

<210> SEQ ID NO 38

-continued

<211> LENGTH: 10
<212> TYPE: PRT
<213> ORGANISM: human

<400> SEQUENCE: 38

Ala Arg Pro Ser Arg Gly Tyr Leu Ala Phe
1 5 10

<210> SEQ ID NO 39
<211> LENGTH: 9
<212> TYPE: PRT
<213> ORGANISM: human

<400> SEQUENCE: 39

Ala Arg Thr Thr Thr Phe Met Leu Val
1 5

<210> SEQ ID NO 40
<211> LENGTH: 9
<212> TYPE: PRT
<213> ORGANISM: human

<400> SEQUENCE: 40

Ala Arg Pro Ser Arg Gly Tyr Leu Ala
1 5

<210> SEQ ID NO 41
<211> LENGTH: 10
<212> TYPE: PRT
<213> ORGANISM: human

<400> SEQUENCE: 41

Cys Arg Lys Met Ala Arg Phe Ser Tyr Ser
1 5 10

<210> SEQ ID NO 42
<211> LENGTH: 10
<212> TYPE: PRT
<213> ORGANISM: human

<400> SEQUENCE: 42

Gln Glu Phe Ala Arg Pro Ser Arg Gly Tyr
1 5 10

<210> SEQ ID NO 43
<211> LENGTH: 9
<212> TYPE: PRT
<213> ORGANISM: human

<400> SEQUENCE: 43

Met Ala Arg Phe Ser Tyr Ser Val Ile
1 5

<210> SEQ ID NO 44
<211> LENGTH: 10
<212> TYPE: PRT
<213> ORGANISM: human

<400> SEQUENCE: 44

Ser Ala Arg Thr Thr Thr Phe Met Leu Val
1 5 10

<210> SEQ ID NO 45
<211> LENGTH: 9
<212> TYPE: PRT

-continued

<213> ORGANISM: human

<400> SEQUENCE: 45

Met Ala Ile Ser Lys Val Phe Glu Leu
1 5

<210> SEQ ID NO 46
<211> LENGTH: 9
<212> TYPE: PRT
<213> ORGANISM: human

<400> SEQUENCE: 46

Phe Ala Arg Pro Ser Arg Gly Tyr Leu
1 5

<210> SEQ ID NO 47
<211> LENGTH: 9
<212> TYPE: PRT
<213> ORGANISM: human

<400> SEQUENCE: 47

Lys Met Val Arg Phe Ser Tyr Ser Val
1 5

<210> SEQ ID NO 48
<211> LENGTH: 9
<212> TYPE: PRT
<213> ORGANISM: human

<400> SEQUENCE: 48

Cys Met Leu Glu Ser Phe Cys Ala Cys
1 5

<210> SEQ ID NO 49
<211> LENGTH: 10
<212> TYPE: PRT
<213> ORGANISM: human

<400> SEQUENCE: 49

Ile Met Ala Ile Ser Lys Ala Phe Glu Leu
1 5 10

<210> SEQ ID NO 50
<211> LENGTH: 10
<212> TYPE: PRT
<213> ORGANISM: human

<400> SEQUENCE: 50

Phe Met Leu Ala Gly Ile Cys Leu Ser Ile
1 5 10

<210> SEQ ID NO 51
<211> LENGTH: 9
<212> TYPE: PRT
<213> ORGANISM: human

<400> SEQUENCE: 51

Val Arg Phe Ser Tyr Ser Val Ile Trp
1 5

<210> SEQ ID NO 52
<211> LENGTH: 9
<212> TYPE: PRT
<213> ORGANISM: human

-continued

<400> SEQUENCE: 52

Cys Arg Lys Met Val Arg Phe Ser Tyr
1 5

<210> SEQ ID NO 53
<211> LENGTH: 10
<212> TYPE: PRT
<213> ORGANISM: human

<400> SEQUENCE: 53

Val Arg Phe Ser Tyr Ser Val Ile Trp Ile
1 5 10

<210> SEQ ID NO 54
<211> LENGTH: 10
<212> TYPE: PRT
<213> ORGANISM: human

<400> SEQUENCE: 54

Ala Arg Pro Ser Arg Gly Asp Leu Ala Phe
1 5 10

<210> SEQ ID NO 55
<211> LENGTH: 9
<212> TYPE: PRT
<213> ORGANISM: human

<400> SEQUENCE: 55

Ala Arg Pro Ser Arg Gly Asp Leu Ala
1 5

<210> SEQ ID NO 56
<211> LENGTH: 9
<212> TYPE: PRT
<213> ORGANISM: human

<400> SEQUENCE: 56

Ala Arg Thr Thr Thr Phe Met Leu Ala
1 5

<210> SEQ ID NO 57
<211> LENGTH: 10
<212> TYPE: PRT
<213> ORGANISM: human

<400> SEQUENCE: 57

Ile Arg Pro Arg Ser Ser Gln Arg Val Leu
1 5 10

<210> SEQ ID NO 58
<211> LENGTH: 10
<212> TYPE: PRT
<213> ORGANISM: human

<400> SEQUENCE: 58

Cys Arg Lys Met Val Arg Phe Ser Tyr Ser
1 5 10

<210> SEQ ID NO 59
<211> LENGTH: 10
<212> TYPE: PRT
<213> ORGANISM: human

<400> SEQUENCE: 59

-continued

Gln Arg Val Leu Pro Met Gly Ile Gln His
1 5 10

<210> SEQ ID NO 60
<211> LENGTH: 9
<212> TYPE: PRT
<213> ORGANISM: human

<400> SEQUENCE: 60

Arg Pro Arg Ser Ser Gln Arg Val Leu
1 5

<210> SEQ ID NO 61
<211> LENGTH: 9
<212> TYPE: PRT
<213> ORGANISM: human

<400> SEQUENCE: 61

Met Ala Ile Ser Lys Ala Phe Glu Leu
1 5

<210> SEQ ID NO 62
<211> LENGTH: 9
<212> TYPE: PRT
<213> ORGANISM: human

<400> SEQUENCE: 62

Phe Ala Arg Pro Ser Arg Gly Asp Leu
1 5

<210> SEQ ID NO 63
<211> LENGTH: 9
<212> TYPE: PRT
<213> ORGANISM: human

<400> SEQUENCE: 63

Gly Ile Cys Leu Ser Ile Gln Ser Tyr
1 5

<210> SEQ ID NO 64
<211> LENGTH: 10
<212> TYPE: PRT
<213> ORGANISM: human

<400> SEQUENCE: 64

Leu Val Ala Gly Leu Gly His Gln Glu Phe
1 5 10

<210> SEQ ID NO 65
<211> LENGTH: 10
<212> TYPE: PRT
<213> ORGANISM: human

<400> SEQUENCE: 65

Asp Thr Trp Leu Pro Lys Lys Cys Ser Leu
1 5 10

<210> SEQ ID NO 66
<211> LENGTH: 9
<212> TYPE: PRT
<213> ORGANISM: human

<400> SEQUENCE: 66

Ala Ile Arg Pro Arg Ser Ser Gln Arg
1 5

-continued

<210> SEQ ID NO 67
<211> LENGTH: 9
<212> TYPE: PRT
<213> ORGANISM: human

<400> SEQUENCE: 67

Val Ile Trp Ile Met Ala Ile Ser Lys
 1               5

<210> SEQ ID NO 68
<211> LENGTH: 9
<212> TYPE: PRT
<213> ORGANISM: human

<400> SEQUENCE: 68

Cys Leu Asn Gly Gly Thr Cys Met Leu
 1               5

<210> SEQ ID NO 69
<211> LENGTH: 9
<212> TYPE: PRT
<213> ORGANISM: human

<400> SEQUENCE: 69

Glu Phe Ala Arg Pro Ser Arg Gly Tyr
 1               5

<210> SEQ ID NO 70
<211> LENGTH: 9
<212> TYPE: PRT
<213> ORGANISM: human

<400> SEQUENCE: 70

Arg Val Pro Pro Met Gly Ile Gln His
 1               5

<210> SEQ ID NO 71
<211> LENGTH: 9
<212> TYPE: PRT
<213> ORGANISM: human

<400> SEQUENCE: 71

Lys Val Phe Glu Leu Gly Leu Val Ala
 1               5

<210> SEQ ID NO 72
<211> LENGTH: 9
<212> TYPE: PRT
<213> ORGANISM: human

<400> SEQUENCE: 72

Met Leu Ala Gly Ile Cys Leu Ser Ile
 1               5

<210> SEQ ID NO 73
<211> LENGTH: 9
<212> TYPE: PRT
<213> ORGANISM: human

<400> SEQUENCE: 73

Arg Val Leu Pro Met Gly Ile Gln His
 1               5

-continued

<210> SEQ ID NO 74
<211> LENGTH: 9
<212> TYPE: PRT
<213> ORGANISM: human

<400> SEQUENCE: 74

Met Gly Ile Gln His Ser Lys Glu Leu
1               5

<210> SEQ ID NO 75
<211> LENGTH: 9
<212> TYPE: PRT
<213> ORGANISM: human

<400> SEQUENCE: 75

Leu Val Met Asp Glu His Leu Val Ala
1               5

<210> SEQ ID NO 76
<211> LENGTH: 9
<212> TYPE: PRT
<213> ORGANISM: human

<400> SEQUENCE: 76

Leu Val Ala Ser Arg Thr Pro Glu Leu
1               5

<210> SEQ ID NO 77
<211> LENGTH: 9
<212> TYPE: PRT
<213> ORGANISM: human

<400> SEQUENCE: 77

Tyr Ser Val Ile Trp Ile Met Ala Ile
1               5

<210> SEQ ID NO 78
<211> LENGTH: 9
<212> TYPE: PRT
<213> ORGANISM: human

<400> SEQUENCE: 78

Trp Leu Pro Lys Lys Cys Ser Leu Cys
1               5

<210> SEQ ID NO 79
<211> LENGTH: 9
<212> TYPE: PRT
<213> ORGANISM: human

<400> SEQUENCE: 79

Leu Gly Leu Val Ala Gly Leu Gly His
1               5

<210> SEQ ID NO 80
<211> LENGTH: 9
<212> TYPE: PRT
<213> ORGANISM: human

<400> SEQUENCE: 80

Phe Arg Asp Asp Ser Ile Trp Pro Gln
1               5

<210> SEQ ID NO 81
<211> LENGTH: 9

-continued

<212> TYPE: PRT
<213> ORGANISM: human

<400> SEQUENCE: 81

Trp Ile Met Ala Ile Ser Lys Val Phe
1 5

<210> SEQ ID NO 82
<211> LENGTH: 9
<212> TYPE: PRT
<213> ORGANISM: human

<400> SEQUENCE: 82

Met Leu Val Gly Ile Cys Leu Ser Ile
1 5

<210> SEQ ID NO 83
<211> LENGTH: 9
<212> TYPE: PRT
<213> ORGANISM: human

<400> SEQUENCE: 83

Val Gly Ile Cys Leu Ser Ile Gln Ser
1 5

<210> SEQ ID NO 84
<211> LENGTH: 9
<212> TYPE: PRT
<213> ORGANISM: human

<400> SEQUENCE: 84

Ile Trp Ile Met Ala Ile Ser Lys Val
1 5

<210> SEQ ID NO 85
<211> LENGTH: 9
<212> TYPE: PRT
<213> ORGANISM: human

<400> SEQUENCE: 85

Leu Val Gly Ile Cys Leu Ser Ile Gln
1 5

<210> SEQ ID NO 86
<211> LENGTH: 9
<212> TYPE: PRT
<213> ORGANISM: human

<400> SEQUENCE: 86

Phe Met Leu Val Gly Ile Cys Leu Ser
1 5

<210> SEQ ID NO 87
<211> LENGTH: 9
<212> TYPE: PRT
<213> ORGANISM: human

<400> SEQUENCE: 87

Trp Ile Met Ala Ile Ser Lys Ala Phe
1 5

<210> SEQ ID NO 88
<211> LENGTH: 9
<212> TYPE: PRT
<213> ORGANISM: human

-continued

<400> SEQUENCE: 88

Met Val Arg Phe Ser Tyr Ser Val Ile
 1               5

<210> SEQ ID NO 89
<211> LENGTH: 9
<212> TYPE: PRT
<213> ORGANISM: human

<400> SEQUENCE: 89

Phe Met Leu Ala Gly Ile Cys Leu Ser
 1               5

<210> SEQ ID NO 90
<211> LENGTH: 9
<212> TYPE: PRT
<213> ORGANISM: human

<400> SEQUENCE: 90

Val Leu Pro Met Gly Ile Gln His Ser
 1               5

<210> SEQ ID NO 91
<211> LENGTH: 9
<212> TYPE: PRT
<213> ORGANISM: human

<400> SEQUENCE: 91

Ile Trp Ile Met Ala Ile Ser Lys Ala
 1               5

<210> SEQ ID NO 92
<211> LENGTH: 9
<212> TYPE: PRT
<213> ORGANISM: human

<400> SEQUENCE: 92

Ile Met Ala Ile Ser Lys Ala Phe Glu
 1               5

<210> SEQ ID NO 93
<211> LENGTH: 10
<212> TYPE: PRT
<213> ORGANISM: human

<400> SEQUENCE: 93

Gly Arg Asn Cys Glu His Asp Val Arg Lys
 1               5                  10

<210> SEQ ID NO 94
<211> LENGTH: 10
<212> TYPE: PRT
<213> ORGANISM: human

<400> SEQUENCE: 94

Ser Arg Thr Pro Glu Leu Pro Pro Ser Ala
 1               5                  10

<210> SEQ ID NO 95
<211> LENGTH: 968
<212> TYPE: DNA
<213> ORGANISM: human

<400> SEQUENCE: 95

-continued

```
cgtccaaggc cgaaagccct ccagtttccc ctggacgcct tgctcctgct tctgctacga      60

ccttctgggg aaaacgaatt tctcattttc ttcttaaatt gccattttcg ctttaggaga     120

tgaatgtttt cctttggctg ttttggcaat gactctgaat taaagcgatg ctaacgcctc     180

ttttccccct aattgttaaa agctatggac tgcaggaaga tggcccgctt ctcttacagt     240

gtgatttgga tcatggccat ttctaaagcc tttgaactgg gattagttgc cgggctgggc     300

catcaggaat ttgctcgtcc atctcgggga tacctggcct tcagagatga cagcatttgg     360

ccccaggagg agcctgcaat tcggcctcgg tcttcccagc gtgtgccgcc catggggata     420

cagcacagta aggagctaaa cagaacctgc tgcctgaatg gggaacctg catgctgggg      480

tccttttgtg cctgccctcc ctccttctac ggacggaact gtgagcacga tgtgcgcaaa     540

gagaactgtg ggtctgtgcc ccatgacacc tggctgccca agaagtgttc cctgtgtaaa     600

tgctggcacg gtcagctccg ctgctttcct caggcatttc tacccggctg tgatggcctt     660

gtgatggatg agcacctcgt ggcttccagg actccagaac taccaccgtc tgcacgtact     720

accactttta tgctagttgg catctgcctt tctatacaaa gctactatta atcgacattg     780

acctatttcc agaaatacaa ttttagatat catgcaaatt tcatgaccag taaaggctgc     840

tgctacaatg tcctaactga aagatgatca tttgtagttg ccttaaaata atgaatacaa     900

tttccaaaat ggtctctaac atttccttac agaactactt cttacttctt tgccctgccc     960

tctcccaa                                                              968
```

<210> SEQ ID NO 96
<211> LENGTH: 188
<212> TYPE: PRT
<213> ORGANISM: human

<400> SEQUENCE: 96

```
Met Asp Cys Arg Lys Met Ala Arg Phe Ser Tyr Ser Val Ile Trp Ile
 1               5                  10                  15

Met Ala Ile Ser Lys Ala Phe Glu Leu Gly Leu Val Ala Gly Leu Gly
            20                  25                  30

His Gln Glu Phe Ala Arg Pro Ser Arg Gly Tyr Leu Ala Phe Arg Asp
        35                  40                  45

Asp Ser Ile Trp Pro Gln Glu Glu Pro Ala Ile Arg Pro Arg Ser Ser
    50                  55                  60

Gln Arg Val Pro Pro Met Gly Ile Gln His Ser Lys Glu Leu Asn Arg
65                  70                  75                  80

Thr Cys Cys Leu Asn Gly Gly Thr Cys Met Leu Gly Ser Phe Cys Ala
                85                  90                  95

Cys Pro Pro Ser Phe Tyr Gly Arg Asn Cys Glu His Asp Val Arg Lys
            100                 105                 110

Glu Asn Cys Gly Ser Val Pro His Asp Thr Trp Leu Pro Lys Lys Cys
        115                 120                 125

Ser Leu Cys Lys Cys Trp His Gly Gln Leu Arg Cys Phe Pro Gln Ala
    130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Thr Phe Met
                165                 170                 175

Leu Val Gly Ile Cys Leu Ser Ile Gln Ser Tyr Tyr
            180                 185
```